(12) United States Patent
Kiuchi

(10) Patent No.: US 6,550,333 B1
(45) Date of Patent: Apr. 22, 2003

(54) SLIDING ROTATION MEMBER FOR TOROIDAL CONTINUOUSLY VARIABLE TRANSMISSION AND EVALUATION METHOD

(75) Inventor: Akihiro Kiuchi, Fujisawa (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 10/246,108
(22) Filed: Sep. 17, 2002

Related U.S. Application Data

(63) Continuation of application No. PCT/JP02/00283, filed on Jan. 17, 2002.

(30) Foreign Application Priority Data

Jan. 17, 2001 (JP) ............................. 2001-009269

(51) Int. Cl.[7] .................................................. G01N 29/04
(52) U.S. Cl. ........................................................ 73/593
(58) Field of Search ......................... 73/593, 618, 620, 73/622, 632, 633, 635, 660

(56) References Cited

U.S. PATENT DOCUMENTS 5,005,417 A * 4/1991 Kawasaki et al. ............ 73/593
5,580,328 A    12/1996 Aramaki
6,113,514 A    9/2000 Okubo et al.

FOREIGN PATENT DOCUMENTS

| JP | 2000-130447 A | 5/2000 |
| JP | 2000-257687 A | 9/2000 |
| JP | 2000-274505 A | 10/2000 |

* cited by examiner

Primary Examiner—Richard A. Moller
(74) Attorney, Agent, or Firm—Christensen O'Connor Johnson Kindness PLLC

(57) ABSTRACT

There is disclosed a sliding rotation member which is rotatably supported by a support shaft in a toroidal continuously variable transmission, and slides on another member, wherein a maximum shear stress depth generated at a maximum deceleration time of the toroidal continuously variable transmission is defined as $Z_0$, a size of a defect obtained in accordance with a shape of the defect detected by a nondestructive inspection method is defined as a square root length, and then a defect of 0.05 mm or more in terms of the square root length is not included in a range of a depth from the surface which is twice the depth $Z_0$.

15 Claims, 11 Drawing Sheets

SLIDING ROTATION MEMBER FOR TOROIDAL CONTINUOUSLY VARIABLE TRANSMISSION AND EVALUATION METHOD

CROSS-REFERENCE TO RELATED APPLICATIONS

This is a Continuation Application of PCT Application No. PCT/JP02/00283, filed Jan. 17, 2002, which was not published under PCT Article 21(2) in English.

This application is based upon and claims the benefit of priority from the prior Japanese Patent Application No. 2001-009269, filed Jan. 17, 2001, the entire contents of which are incorporated herein by reference.

BACKGROUND OF THE INVENTION

1. Field of the Invention

The present invention relates to sliding rotation members for highly reliable continuously variable transmission (CVT) for use in a toroidal CVT, such as a disk and power roller bearing, and an evaluation method of the members.

2. Description of the Related Art

For an input/output disk and power roller bearing for use in a toroidal continuously variable transmission (CVT), whose use environments include a high load and high surface pressure and which are positioned with important protective components, there have been proposed a large number of techniques for enhancement of durability in order to prevent breakage and flaking in a short time. For example, in Jpn. Pat. Appln. KOKAI Publication No. 2001-032900 (hereinafter referred to as Prior Document 1), there are disclosed chemical components of alloy steels for use in the input/output disk and power roller bearing, and a carbon amount, nitrogen amount, surface hardness, and the like of a function surface are limited, and preferable alloy components, heat treatment quality, and the like for enhancing the durability.

Moreover, in Jpn. Pat. Appln. KOKAI Publication No. 2001-026840 (hereinafter referred to as Prior Document 2), it is disclosed that a high-cleanliness steel is used in order to prevent breakage and flaking from being generated starting at a large nonmetal inclusion in a steel in a short time. Furthermore, a method of performing an ultrasonic flaw detection/inspection is used to guarantee that the large nonmetal inclusions do not exist in a traction surface 62 and surface layer portion of the input/output disk shown in FIG. 9, and a traction surface 67 and surface layer portion of an inner ring of the power roller bearing shown in FIG. 10. For example, it is guaranteed that the nonmetal inclusion having a maximum size of 0.1 mm or more does not exist within 0.5 mm from the surface in a disclosed member for CVT.

Moreover, for the use environments of a toroidal continuously variable transmission disk and power roller, high torque transmission capabilities are required from properties described later as compared with other types of continuously variable transmissions. It is necessary to apply a highly durable material which is not broken by a very large bend stress and repeated stress. To solve the problem, the present inventors have developed and proposed a management method of a steel which satisfies durability necessary especially for the CVT disk and power roller in Jpn. Pat. Appln. KOKAI Publication No. 11-193855 (hereinafter referred to as Prior Document 3).

To detect an inner defect of a steel material for use as a material of a bearing ring, only a defect inspection has heretofore been performed by an ultrasonic inspection in a steel manufacturing process. The ultrasonic inspection comprises: transmitting an ultrasonic wave to the inside of a rolled steel material from an outer peripheral surface thereof in water or on a base to detect a flaw. For example, a normal wave method described in "page 31, No. 6, Vol. 46, Tokushuko, Tokushuko Club Association" (hereinafter referred to as Prior Document 4), and the like are known.

In the inspection of defects (nonmetal inclusions) of the steel material in a steel maker, only large defects each having a width of several hundreds of micrometers and a length of several millimeters or more are detected because of the properties of the inspection. Additionally, a representative inspection (sampling inspection) is performed so that the high-cleanliness steel is entirely managed. However, the presence/absence of harmful inclusions has not been grasped or guaranteed with respect to all the steel materials (total inspection) in the existing technique.

Moreover, in recent years, it has been possible to detect even the nonmetal inclusion, for example, having a micro size of about 0.01 mm (10 $\mu$m) using a high frequency in the ultrasonic inspection in a background of progress of a nondestructive inspection technique. However, in the ultrasonic inspection, when the frequency is increased, attenuation of the ultrasonic wave inside the steel material increases, and the method is not practical. Especially when the surface of the steel material becomes rough, the attenuation of the ultrasonic wave further increases. Therefore, for a practical range of the size of the inclusion, in which the total inspection of a product is possible, only a large defect having a width of several hundreds of micrometers and a length of several millimeters or more is detected in the existing circumstances.

The toroidal continuously variable transmission (CVT) disk and power roller bearing member having large defects inside (particularly in the vicinities of surfaces) are sometimes broken in a relatively short time, when repeatedly undergoing bend stresses. Particularly a rolling member of the large CVT repeatedly undergoes a high bend stress, and therefore tends to flaking or crack starting at a position deeper than a maximum stress generated position in which a conventional general-purpose rolling bearing has heretofore undergone the stress. Concretely, in input/output disks 31, 32 of the large CVT, a large repeated bend stress is added to portions (traction surface 62 and surface layer portion) shown by diagonal lines in FIG. 11, and a high tensile stress is generated. Moreover, in the inner ring of the power roller bearing of the large CVT, the large repeated bend stress is added to portions (traction surface 67, inner peripheral surface 68, rolling surface 69, and surface layer portion) shown by the diagonal lines in FIG. 12, and the high tensile stress is generated. Therefore, the flaking or cracks are easily generated starting at these surfaces 62, 67, 68, 69 and surface layer portions.

Additionally, in Prior Document 1 described above, it is proposed that the alloy components are optimized and heat treatment quality is specified in order to prevent the generation of the flaking or cracks. Moreover, in the invention of Prior Document 1, the traction surfaces 62 and surface layer portions of the input/output disks 31, 32 shown in FIG. 11 are strengthened, and the traction surfaces 67, inner peripheral surfaces 68, rolling surfaces 69, and surface layer portions of power roller inner rings 36*a*, 37*a* shown in FIG. 12 are strengthened, so that the entire strength is enhanced. However, it is not proposed to improve the large inclusion at which the flaking or crack starts.

Moreover, in Prior Document 2 described above, it is proposed that among the traction surfaces 62, inner peripheral surfaces 63, and surface layer portions of the input/output disks 31, 32 shown in FIG. 11, and the traction surfaces 67, inner peripheral surfaces 68, and rolling surfaces 69 of the power roller inner rings 36a, 37a shown in FIG. 12, particularly the large inclusions of the surface layer portions corresponding to the traction surfaces 62, 67 are detected and guaranteed in order to prevent the breakage or the flaking in the short time. However, in the invention of Prior Document 2, only the surface layer portions of the traction surfaces 62, 67 are objects of a precision inspection (or the total inspection), but the surface layer portions of the surfaces 63, 68, 69 other than the traction surfaces are not the objects of the precision inspection (or the total inspection).

A future demand for the CVT lies not only in long life and breakage prevention of the disk and power roller but also in eradication of accidental generation of a short-life bearing. This is a demand for a highly reliable member for the CVT which has no possibility of generation of short-life components even under conditions further stricter than before, with future elongation of guarantee period of a car.

The present invention has been developed to solve the above-described problems, and an object thereof is to provide a long-life sliding rotation member for CVT in which flaking is not easily generated in a sliding surface, and an evaluation method of a highly reliable sliding rotation member for CVT in which it is possible to detect all defects (particularly, nonmetal inclusions) existing particularly in a surface layer portion of an inner-diameter end in which a stress rises during operation of a CVT constituting member with a high precision.

BRIEF SUMMARY OF THE INVENTION

One of characteristics of a toroidal CVT is that the CVT can bear a larger input torque than other CVTs (e.g., a belt CVT) can. With a car of a large engine displacement as an object in which a large torque is generated, the toroidal CVT receives a larger input torque. The toroidal CVT is of a type such that a large load can be received as compared with the belt CVT, and therefore a higher load and surface pressure are applied to a disk and power roller. In the future it is expected that a portion undergoing a repeated bend fatigue is positioned more deeply in the toroidal CVT.

In Prior Document 2, the present inventors have proposed that the nonmetal inclusion existing within 0.5 mm right under the traction surface and having a maximum diameter of 0.1 mm or more is limited and this can prevent the member from breaking. That is, as a result of intensive researches, the present inventors have found that the nonmetal inclusion (defect) existing within 0.5 mm from the traction surface and having a maximum diameter of 0.1 mm or more is a start point of bend fatigue destruction of a CVT component, and have proposed concrete solution means in Prior Document 2 based on the finding.

However, as a result of the subsequent research, it has been found that the bend fatigue destruction (hereinafter referred to simply as "breakage") is generated with a stricter use condition of the toroidal CVT component even in a position of the nonmetal inclusion deeper than the position described in Prior Document 2 described above. That is, as a result of the research under a stress condition stricter than a conventional condition, the present inventors have found that the breakage is sometimes generated even in a position deeper than the depth disclosed in Prior Document 2 and that the breakage is sometimes generated even in a defect smaller than the defect with the size disclosed in Document 2.

Then, the present inventors have intensively researched a relation between the input torque and breakage and the size of the nonmetal inclusion. As a result, it has been found that the defect having a square root length of 0.1 mm or more (more preferably 0.05 mm or more) is prevented from existing in a region within twice a depth of a position ($Z_0$) of maximum shear stress undergone by the toroidal CVT component, and this can prevent the toroidal CVT component from breaking.

Moreover, the sliding surface undergoes rolling fatigue between the disk and power roller. When the large nonmetal inclusion exists right under the sliding surface, there is a problem that the flaking is generated with the short life. When the toroidal CVT component flaking, a trouble is generated in the running of a car. Therefore, it is important to lengthen the life against the rolling fatigue and eradicate short-life components. In order to solve the problems, as a result of the intensive research of the relation between the input torque and flaking and the size of the nonmetal inclusion, the present inventors have found that the elimination of the nonmetal inclusion having a square root length of 0.05 mm or more within twice the depth ($Z_0$) of maximum shear stress undergone by the toroidal CVT component can prevent the component from peeling in a short time.

On the other hand, the present inventors have noted the ultrasonic inspection as a method of evaluating the nonmetal inclusion existing under the sliding surface of the disk and power roller bearing of the CVT, and have made intensive efforts in the improvement of the inspection method. As a result, it has been found that it is possible to detect the nonmetal inclusion of 0.1 mm or less existing within 0.5 mm from the surface with application of an angle wave method (surface wave method), and this has been disclosed in Prior Document 2 described above. However, a main object of the invention disclosed in Prior Document 2 is to detect the defect in a relatively shallow position within 0.5 mm from the surface. Therefore, with twice the depth ($Z_0$) of the present invention, for example, a depth of 2 mm to 3 mm is an object depending on the size of the input torque. Therefore, it is necessary to also detect the defects (including the nonmetal inclusion, macro-streak flaw, and open crack) each having a square root length of 0.05 mm or more or 0.1 mm or more in a position of a depth six times a conventional object depth.

Prior Document 2 described above discloses a method of detecting the defect in the depth of 0.5 mm under the surface. Furthermore, the present inventors have intensively researched the ultrasonic inspection in which the portion having a depth of 0.5 mm or more under the surface can be inspected with a high precision, and have completed the present invention.

According to the present invention, there is provided a toroidal continuously variable transmission comprising: an input disk disposed on an input shaft; an output disk disposed on an output shaft; and a power roller bearing which includes an inner ring, an outer ring and a plurality of rolling members, in which the inner ring is rollingly contacted in the input disk and output disk and which transmits a power of the input shaft to the output shaft, wherein a maximum shear stress depth obtained on a condition on which the input disk is rolling contacted in the inner ring of the power roller bearing in a maximum deceleration state of the toroidal continuously variable transmission and the power is transmitted is defined as a symbol Zo, a size of a defect obtained in accordance with a shape of the defect detected by a nondestructive inspection method is defined as a square root length, and then at least one of the input disk and the inner ring of the power roller bearing does not include a defect of 0.05 mm or more in terms of the square root length in a range of a depth from a traction surface which is twice the above-described Zo.

According to the present invention, there is provided a sliding rotation member for a toroidal continuously variable transmission, which is rotatably supported by a support shaft in the toroidal continuously variable transmission, and slides on another member, wherein a maximum shear stress depth generated at a maximum deceleration time of the toroidal continuously variable transmission is defined as $Z_0$, a size of a defect obtained in accordance with a shape of the defect detected by a nondestructive inspection method is defined as a square root length, and then a defect of 0.05 mm or more in terms of the square root length is not included in a range of a depth from the surface of the sliding rotation member which is twice the above-described $Z_0$.

The defect includes a nonmetal inclusion, macro-streak flaw, and opening crack. Since most of the defects detected from CVT components are the nonmetal inclusions, it is essential to prevent large nonmetal inclusions from existing in portions shown by diagonal lines in FIGS. 7, 8. In general, the large nonmetal inclusion has a maximum diameter of 0.05 mm or more, and there are nonmetal inclusions having various shapes. Therefore, the size of the defect is defined by the square root length entirely in the present invention.

Here, the "square root length" is obtained in the following 1) and 2) in accordance with the shape of the defect.

1) When the shape of the defect is linear (linear defect), a square root $(L \times D)^{1/2}$ of a product of length L and width D of the defect is defined as the square root length.

2) When the shape of the defect is granular, spherical, or clumpy (nonlinear defect), a square root $(D1 \times D2)^{1/2}$ of a product of maximum diameter (long-axis diameter) D1 and minimum diameter (short-axis diameter) D2 of the defect is defined as the square root length.

According to a first aspect of the present invention, when the surface of the sliding rotation member (the input disk, the inner ring of the power roller bearing) is a rolling contact surface (traction surface), the defect existing in the range of the depth from the rolling contact surface (traction surface) twice the maximum shear stress depth $Z_0$ is an object. The defect is detected using a combination of a surface wave method, angle wave method, and normal wave method, acceptance/rejection is judged based on the detected result, and a defect of 0.10 mm or more in terms of the square root length is prevented from being included in the portion of the depth range (claim 1). In this case, it is more preferable on quality assurance to prevent the defect of 0.05 mm or more (particularly the nonmetal inclusion) from being included (claim 2).

Moreover, when the another member is the inner ring of the power roller bearing, that is, when the sliding rotation member is the input disk or the output disk, as shown in FIG. 7, it is preferable not to include a defect exceeding 0.20 mm in terms of the square root length (particularly the nonmetal inclusion) in a portion in at least a half depth L1 of a diametric length of an end surface on an inner peripheral surface side and in at least one-third depth C/3 of an axial length of the inner peripheral surface from an end surface side (claim 3).

Furthermore, the another member is an input or output disk, that is, the sliding rotation member is a power roller bearing inner ring. In this case, as shown in FIG. 8, it is preferable not to include a defect exceeding 0.20 mm in terms of a square root length (particularly the nonmetal inclusion) in a portion in a depth L2 which is at least a half of a diametric length of the end surface from an inner peripheral surface side and in a depth F/2 which is at least a half of the axial length of the inner peripheral surface from an end surface side (claim 4).

According to the present invention, there is provided an evaluation method of a sliding rotation member for a toroidal continuously variable transmission, comprising: immersing the sliding rotation member rotatably supported by a support shaft in the toroidal continuously variable transmission and slid on another member during use together with an ultrasonic probe into a transmission medium; allowing an ultrasonic wave to be incident upon the sliding rotation member from the ultrasonic probe via the transmission medium; and evaluating defects existing in the surface and an inner portion of the sliding rotation member based on a waveform of ultrasonic echo reflected from the sliding rotation member, the method comprising:

(a) a step of using at least one of a surface wave method and angle wave method to scan the surface of the sliding rotation member and a portion right under the surface;

(b) a step of defining a maximum shear stress depth generated inside the sliding rotation member at a maximum deceleration time of the toroidal continuously variable transmission as depth $Z_0$, and using at least one of the angle wave method and a normal wave method to scan a portion of a depth from the surface which is twice the maximum shear stress depth $Z_0$; and (c) a step of defining a size of the defect obtained in accordance with a shape of the defect as a square root length, judging the sliding rotation member to be rejected, when the square root length of the defect detected by the steps (a) and (b) is 0.10 mm or more (preferably 0.05 mm or more), and judging the sliding rotation member to be accepted, when the square root length of the defect detected by the steps (a) and (b) is less than 0.10 mm (preferably less than 0.05 mm).

The surface (incidence surface) upon which the ultrasonic wave is incident is a traction surface or end surface of the sliding rotation member. The traction surface is a surface which undergoes a dynamic repeated stress by a mutual sliding contact with the other members.

When the sliding rotation member is the input or output disk, the ultrasonic wave is transmitted into the sliding rotation member from the end surface (claim 5). The end surface is positioned between the inner peripheral surface brought into contact with or disposed opposite to the support shaft and the traction surface, and substantially crosses at right angles to the support shaft. As shown in FIGS. 15 and 16, ultrasonic waves 4 are transmitted into a portion in a half (L1) of the diametric length W of an end surface 70 from an inner peripheral surface 63 side and a depth C/3 which is at least ⅓ of the axial length of the inner peripheral surface 63 from an end surface 70 side, and a surface layer portion right under the end surface 70 and inner peripheral surface 63 is scanned.

Also when the sliding rotation member is the inner ring of the power roller bearing, the ultrasonic wave is transmitted into the sliding rotation member from the end surface (claim 6). The end surface is in a position defined by the inner peripheral surface brought into contact with or disposed opposite to a pivot shaft 50, pivot shaft, and rolling groove, and substantially crosses at right angles to the pivot shaft. As shown in FIGS. 17 and 18, the ultrasonic waves 4 are transmitted into a portion in a half (L2) of a diametric length G of an end surface 75 from an inner peripheral surface 68 side and a depth F/2 which is at least a half of the axial length of the inner peripheral surface 68 from an end surface 75 side, and the surface layer portion right under the end surface 75 and inner peripheral surface 68 is scanned.

In this case, it is preferable to use an ultrasonic wave with a predetermined frequency in a range of 5 MHz to 30 MHz in the steps (a) and (b). It is further preferable to use an ultrasonic wave with the predetermined frequency in a range of 5 MHz to 15 MHz in the step (a) and to use an ultrasonic wave with the predetermined frequency in a range of 10 MHz to 25 MHz in the step (b).

In a concrete example, the angle wave method or the surface wave method is used in inspecting the depth of 0.5 mm from the surface, and the defect is detected in a frequency range of 5 MHz to 30 MHz, preferably 5 MHz to 15 MHz. Furthermore, the angle wave method or the normal wave method is used in inspecting a depth exceeding 0.5 mm from the surface in which the ultrasonic wave is attenuated inside the material and it is difficult to detect the defect.

Moreover, in the concrete example, when a range of a depth exceeding 0.5 mm from the surface and twice the maximum shear stress depth $Z_0$ (practically a depth of 2 to 3 mm) is inspected, the angle wave method or the normal wave method is used to detect the defect in a frequency range of 5 MHz to 30 MHz, preferably 10 MHz to 25 MHz. When both methods are combined, the above-described problem can be solved.

Additionally, a method for use in detecting the deep range is generally the normal wave method (immersion method), but a position shallower than 0.5 mm is a region (dead band) which cannot be detected by the surface echo to reflect a sonic wave on the surface, and the defect cannot be detected in the normal wave method. To solve the problem, the present inventors have found an optimum method in which the ultrasonic wave is transmitted from the specific surface and a CVT member is highly precisely scanned in order to detect the nonmetal inclusion existing in a surface layer region right under the surface.

It has heretofore been the that a detection limit in ultrasonic inspection is generally a ½ wavelength, but according to the method of the present invention, it is possible to detect the defect having a square root length of 0.05 mm in the vicinity of the surface. However, in this case, it is difficult to detect the defect having a target size in a frequency of 5 MHz or less. Moreover, with a frequency exceeding 30 MHz, the sonic wave is largely attenuated, and it is difficult to detect the flaw in the target depth. Therefore, a flaw detection frequency is limited to a range of 5 MHz to 30 MHz. Furthermore, a frequency of 5 MHz to 15 MHz is preferable in a range of 0.5 mm from the surface, and a frequency of 10 MHz to 25 MHz is preferable in a range of 0.5 mm to twice the maximum shear stress depth $Z_0$ (practically a depth of 2 to 3 mm). When the ultrasonic wave of the specific frequency range is selectively used in accordance with the flaw detection depth, a detection intensity having a desired magnitude is maximized. The above-described method is suitable for scanning the portion which undergoes a high bend stress other than the traction surface.

(Action)

The toroidal continuously variable transmission (CVT) is used in an environment having high load and surface pressure, and therefore undergoes a load much larger than the general-purpose rolling bearing. Particularly in the input/output disk, the repeated bend stress is applied to the diagonal-line portion in FIG. 11 (the surfaces 62, 63 and the surface layer portion right under the surfaces), and a high tensile stress is generated. Moreover, similarly in the power roller bearing inner ring, the repeated bend stress is applied to the diagonal-line portion in FIG. 12 (the surfaces 67, 68, 69 and the surface layer portion right under the surfaces), and the high tensile stress is generated. Therefore, the input/output disk and power roller bearing inner ring easily flaking and break starting from these portions.

To prevent the flaking and break, in Prior Document 2, there is disclosed the ultrasonic inspection method which guarantees that large nonmetal inclusions do not exist in the traction surface 62 of the input/output disk and the traction surface 67 and surface layer portion right under the surface of the power roller bearing inner ring. However, in the inspection method of Document 2, the portions shallow from the traction surfaces 62, 67 are objects, and the portions further deeper from the traction surface are not the objects. Moreover, in the inspection method of Document 2, only the surface layer portion right under the traction surface is regarded as the object, and other surface layer portions distant from the traction surface are not the objects.

A main use of the toroidal CVT is a car, but if a damage (flaking or breakage) is enerated in the input/output disk or the power roller bearing, the other components in the CVT mechanism are crucially damaged and a serious accident is possibly caused. Particularly, when the input/output disk or the power roller bearing inner ring breaks during the running of the car, there is a possibility of development of a major accident. Therefore, it is necessary to guarantee quality so that these components are inhibited from breaking.

The present inventors have assumed the repeated bend stress applied to the input/output disk and power roller bearing inner ring in an apparatus with the CVT mounted thereon, and have analyzed a stress distribution generated in the respective members by a finite element method (FEM) using computer graphics simulation. As a result, as shown in FIGS. 13, 14, it has been found that high-stress generated regions 71, 76 exist also in the surface layer portions (one end portion of the inner peripheral surface) of the surfaces 63, 68, 69, 71, 75 other than the traction surfaces 62, 67. That is, as shown in FIG. 13, it has been found that local stress concentration easily occurs in the corner edge 71 with the inner peripheral surface 63 intersecting with the end surface 70 therein and the vicinity of the edge in input/output disks 31, 32. As shown in FIG. 14, it has been found that a local stress is easily generated in the corner edge 76 with the inner peripheral surface 68 intersecting with the end surface 75 therein and the vicinity of the edge in power roller bearing inner rings 36a, 37a.

Then the present inventors have noted these high-stress generated regions 71, 76, and have intensively researched correlations of size, depth position, and breakage (flaking) of the large nonmetal inclusion included in the surface layer portion. As a result, it has been found that the large nonmetal inclusions having a square root length of 0.2 mm or more are prevented from being included in regions shown by diagonal lines of FIGS. 7 and 8 and the breakage (flaking) can thereby be prevented regardless of any size of the disk and power roller bearing inner ring. That is, the high-stress generated regions 71 of the input/output disks 31, 32 correspond to the portion 61 shown by diagonal lines in FIG. 7, and the high-stress generated regions 76 of the power roller bearing inner rings 36a, 37a correspond to the portion 66 shown by diagonal lines in FIG. 8.

Additionally, the present inventors have confirmed that the flaking or breakage is not generated during a guaranteed life regardless of the sizes of the input/output disk and power roller bearing, as long as the portions of the regions shown by the diagonal lines in FIGS. 7, 8 have a certain constant cleanliness (substantially have no defect).

Here, the "surface layer portion" includes not only the portion right under the surface but also the portion in a certain degree of depth from the surface and further the surface.

The present inventors have obtained the maximum shear stress depth $Z_0$ from toroidal CVT design conditions in accordance with the following procedure, have used an obtained $Z_0$ value as a reference to apply various ultrasonic inspections such as the normal wave method, angle wave method, and surface wave method to the input/output disk and power roller bearing inner ring, and have checked the methods. As a result, as shown in Table 3, it has been found that the angle wave method is most suitable for the depth from the surface in a range of once or twice $Z_0$ and that the surface wave method and normal wave methods are most suitable for the depth from the surface in a range of twice or more times $Z_0$.

This $Z_0$ of a time at which the input/output disk and power roller bearing inner ring of the toroidal CVT are rotated and brought into contact, and a method of obtaining $Z_0$ will be described with reference to FIGS. 19 and 20.

Since large repeated shear and bend stresses overlap with each other in a composite manner and act on the input/output disk and power roller bearing of the toroidal CVT, a strict stress load state different from that of a general-use rolling bearing is obtained. The position of the CVT constituting member in which the dynamic maximum shear stress is generated is deeper than that of the general-use rolling bearing.

Here, it is assumed that the depth position on which the dynamic maximum shear stress acts is referred to as the "maximum shear stress depth $Z_0$". The maximum shear stress depth $Z_0$ is used in calculating a rolling life of each constituting member, when designing the CVT.

The method of obtaining the maximum shear stress depth $Z_0$ will be described using Hertz's contact theory. When a member 1 elastically contacts a member 2, curvature radii of the members 1, 2 corresponding to a first surface (surface I crossing at right angles in a rotation detection) and a second surface (surface II crossing at right angles in the rotation detection) are represented as $\rho_{11}, \rho_{12}, \rho_{21}, \rho_{22}$. Here, with the application to the contact of a disk (member 1) and power roller (member 2) of a TCVT bearing, the contacts of both the members 1, 2 are given by the following equations (1), (2), (3), (4).

$$a = (50.5 \times 10^{-3}) \mu \cdot (P/\Sigma\rho)^{1/3} \tag{1}$$

$$b = (50.5 \times 10^{-3}) \nu \cdot (P/\Sigma\rho)^{1/3} \tag{2}$$

$$b/a = \{(t^2-1)(2t-1)\}^{1/2} = k_1 \tag{3}$$

$$\cos \tau = |\rho_{11} - \rho_{12} + \rho_{21} - \rho_{22}|/\Sigma\rho \tag{4}$$

Additionally, symbol a denotes a contact ellipse long axis radius, symbol b denotes a contact ellipse short axis radius, symbol $\tau$ denotes an auxiliary angle, symbols $\mu$ and $\nu$ denote constants concerning cost, symbol P denotes a load, and symbol $\Sigma\rho$ ($=\rho_{11}+\rho_{12}+\rho_{21}+\rho_{22}$) denote a sum of main curvatures with which two elastic members form right angles in a contact point.

Moreover, the above-described parameters $\mu$, $\nu$, $k_1$ have the following relation.

$\mu = \{2E(k_2)/\pi k_{12}\}^{1/3}$
$\nu = \{2E(k_2)k_1/\pi\}^{1/3}$
$k_1 = b/a$
$k_2 = (1-k_{12})^{1/2}$

Therefore, the parameters $\mu$, $\nu$ are constants obtained by second class complete ellipse integration.

The contact ellipse long axis radius a is obtained from the above equation (1), and the contact ellipse short axis radius b is obtained from the above equation (2). These are assigned to the above equation (3) and solved concerning a parameter t, and a dynamic maximum shear stress generated position Zo (depth from the surface) is given by the following equation (5). This is described in pages 230 to 240 of "Bearing Lubrication Manual (Daily Industrial Newspaper Co.; edited by Bearing Lubrication Manual Edition Committee; issued in 1961)" (hereinafter referred to as Document 5).

$$Zo = b\{(t+1)(2t-1)^{1/2}\}^{-1} \tag{5}$$

Additionally, the above-described Zo can also be obtained from the relation of the following equation (6) using a maximum contact pressure Pmax.

$$P\max = [188 \times \{P(\Sigma\rho)^2\}^{1/3}]/\mu\nu \tag{6}$$

(Calculation Case Example)

Subsequently, the numeric values of the respective parameters are concretely assigned to the above equations (1) to (6), and the maximum shear stress depth Zo and maximum contact pressure $P_{max}$ are obtained. Each example of the numeric value of each parameter will be described.

Disk radius ro=40 mm

Power roller radius $R_{22}$ =32 mm

Contact angle $\phi$=35.4° (contact condition of the maximum deceleration time of the CVT)

Load P=52200 N

Power roller rotation center distance D=$2r_1$=130 mm

Coefficient ko=$\{(\phi D/2)-ro\}/ro$=0.625

The above-described numeric values are use to obtain the curvature radii $\rho_{11}, \rho_{12}, \rho_{21}, \rho_{22}$. Additionally, for the values of the $\rho_{11}, \rho_{12}, \rho_{21}, \rho_{22}$, fifth digits after the decimal point are rounded off.

$\rho_{11}$=cos $\phi/\{ro(1+ko-\cos \phi)\}$=0.0252

$\rho_{12}$=-1/ro=-0.025

$\rho_{21}$=1/ro=0.025

$\rho_{22}$=1/$R_{22}$=0.0313

Therefore, $\Sigma\rho = \rho_{11}+\rho_{12}+\rho_{21}+\rho_{22}$=0.0565

$|\rho_{11}-\rho_{12}+\rho_{21}-\rho_{22}|$=0.0439

These numeric values are assigned to the above equation (4) and the value of cost is obtained. Additionally, for the value of cost, the third digit after the decimal point is rounded off.

$\cos \tau$=0.0439/0.0565=0.78

An appendix table of Document 5 (ellipse integration table) is used to obtain the parameters $\mu$ and $\nu$ corresponding to $\cos \tau$=0.78. Additionally, an intermediate value not described in the appendix table of Document 5 was calculated by a proportional calculation method.

$\mu$=2.196, $\nu$=0.5581

These values of $\mu$, $\nu$ and values of P, $\Sigma\rho$ are assigned to the above equations (1), (2), and a long axis radius a and a short axis radius b of a contact ellipse are obtained.

$a$=5.05, $b$=1.283

These numeric values are assigned to the above equation (3), and a solution of a cubic equation (real root) is obtained concerning the parameter t.

$t=1.03$

The obtained value of t is assigned to the above equation (5) and the maximum shear stress depth Zo is obtained.

$Zo=0.614$ (mm)

Furthermore, the respective values of $\mu$, $v$, P, $\Sigma\rho$ are assigned to the above equation (6), and the maximum contact pressure $P_{max}$ is obtained.

$P_{max}=4.05$ (GPa)

In the above-described calculation case example, the Zo value is 0.614 mm, and $P_{max}$ value is 4.05 GPa.

As described above, according to the present invention, attention is focused on the inspection of the portion in which destruction most easily occurs in the toroidal CVT member, and thereby the quality of the CVT member can be guaranteed with high precision. Particularly when the optimum ultrasonic inspection is used in accordance with the depth from the surface, the inspection precision of the defect is dramatically enhanced, and therefore a level of quality assurance can be raised.

Moreover, according to the present invention, since the defect included in the CVT member is scanned in a nondestructive manner, the total number of CVT members can be inspected, and it is possible to guarantee the quality with the high reliability. Particularly, in the method of the present invention, the true size and shape of the defect can be grasped based on the echo reflected from the defect. Therefore, the high reliability can be obtained as compared with the conventional method of using a microscope to two-dimensionally observe the defect which appears in a cut surface.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Preferred embodiments of the present invention will be described hereinafter with reference to the accompanying drawings.

Figure 1:
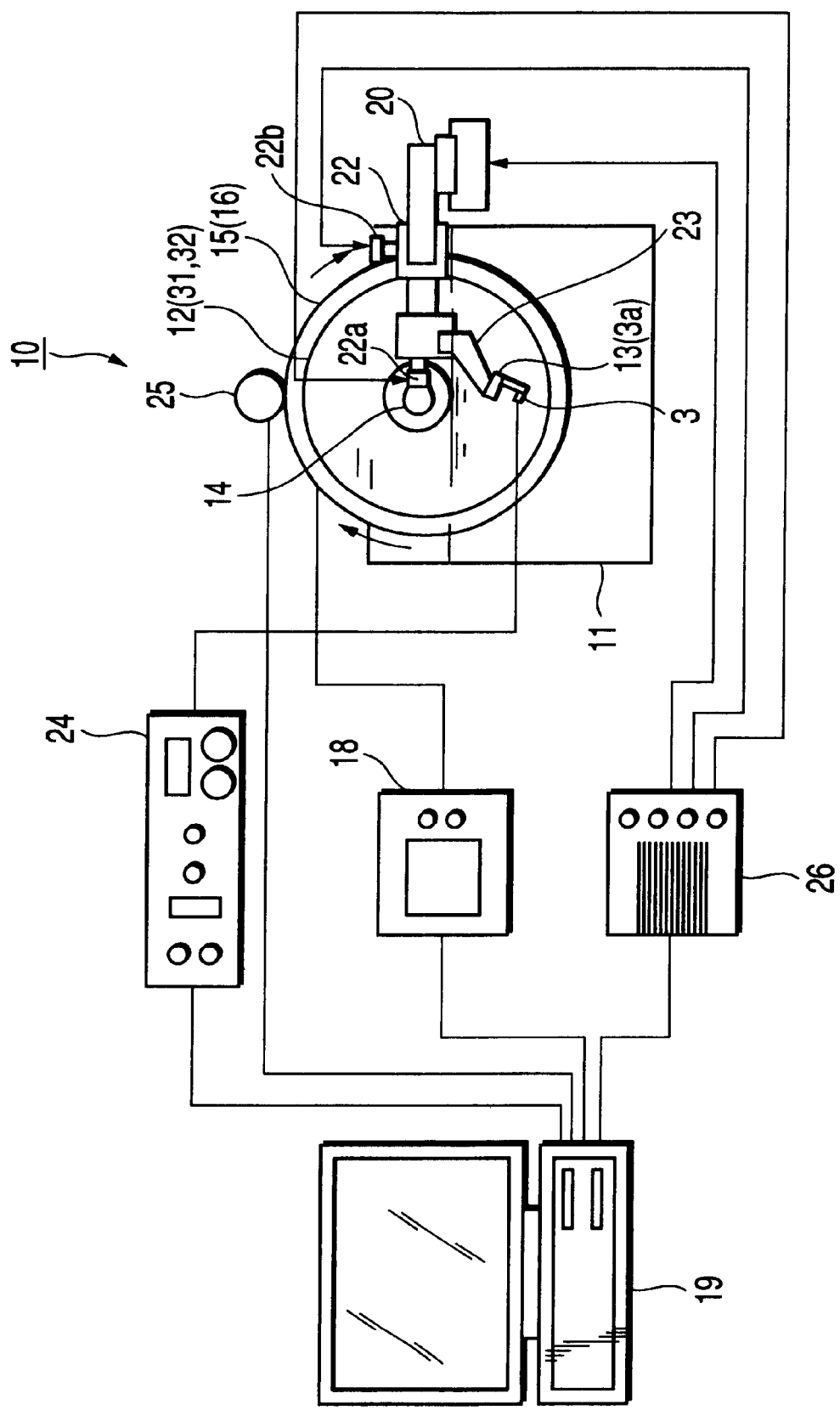
FIG. 1 is a constitution block diagram showing an outline of an evaluation test apparatus.

FIG. 1 is a schematic diagram showing a ultrasonic flaw detection/inspection apparatus. A reference numeral 11 in the drawing denotes a water tank in which water as an ultrasonic transmission medium is pooled. A CVT disk (or may be a power roller bearing inner ring) as an object 2 and an ultrasonic probe 3 are immersed in water and disposed in the water tank 11.

For the ultrasonic probe 3, a focus type probe is used including a focus mechanism which has strong directivity and which is not easily influenced by a curvature of the object 2 (31, 32, 36a, 37a). The focus type probe has a high S/N ratio. The object 2 is disposed on a turntable 15 (16) while a disk surface is directed on the side of the probe 3. The axis of the object 2 is the same as the rotation axis of the turntable 15 (16), and both members are synchronously rotated/drive by a servo motor 14. Additionally, a reference numeral 18 denotes a control amplifier for driving the servo motor 14.

Figure 2:
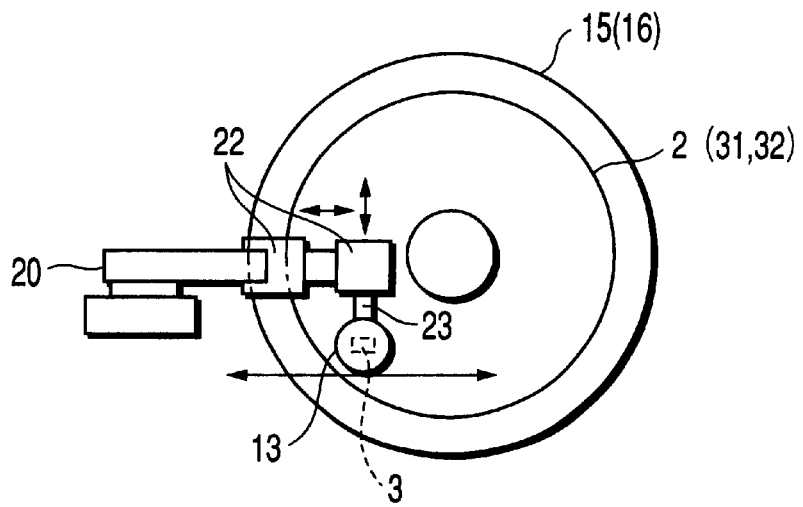
FIG. 2 is an enlarged front view showing a main part and CVT power disk of the evaluation test apparatus.
Figure 3:
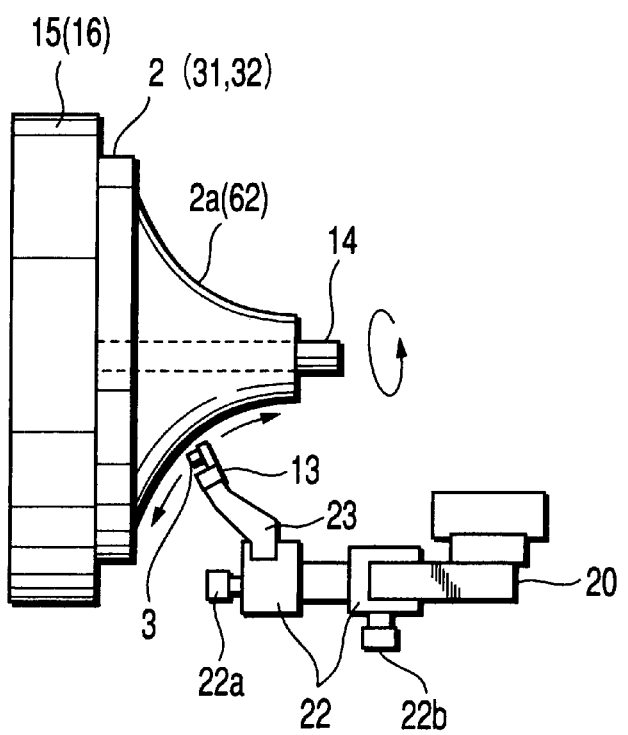
FIG. 3 is an enlarged side view showing the main part and CVT power disk of the evaluation test apparatus.

As shown in FIGS. 2 and 3, the probe 3 is attached to the tip end of a swing arm 23 via an attachment plate 13. The swing arm 23 is supported by an XY table 22 which can move both in a radius direction and axial direction of the object 2 under two-axes control. The XY table 22 includes two drivers 22a, 22b controlled by a controller 26. These drivers 22a, 22b allow the probe 3 together with the XY table 22 to move along a sliding surface 2a (62) of the object 2 (31, 32).

Furthermore, the XY table 22 is movably supported by a linear guide apparatus 20. The linear guide apparatus 20 moves the probe 3 for ultrasonic inspection in the axial direction via a servo motor (not shown) controlled by the controller 26 for linear guide. When a rotary encoder 25 disposed on the outer peripheral surface of the object 2 detects one rotation (360°) of the object 2, the controller 26 for linear guide controls the servo motor based on an instruction from a control apparatus 19 and moves the probe 3 by a predetermined distance in the axial direction of the object 2. Thereby, the whole section of the object 2 is searched for detecting defects.

Additionally, in angle wave method, the probe 3 may be moved in parallel on the diameter (passed through a center) of the object 2 in accordance with an angle with an offset of plus/minus several millimeters. Moreover, the probe 3 may be swung on the diameter of the object 2.

The probe 3 is connected to both input and output portions of an ultrasonic flaw detection apparatus 24. The probe 3 transmits an ultrasonic pulse to the outer peripheral surface 2a of the object in accordance with a voltage signal from the ultrasonic flaw detection apparatus 24, receives reflected echo, converts the echo to the voltage signal and sends the signal back to the ultrasonic inspection apparatus 24.

The ultrasonic inspection apparatus 24 transmits an instruction signal including the voltage signal to the probe 3 for ultrasonic probing based on the instruction from the personal computer 19 as the control apparatus, and sends flaw detection information obtained based on transmitted and received signals back to the control apparatus 19. Thereby, the control apparatus 19 displays a waveform of ultrasonic echo on a CRT screen.

The probe 3 moves by a predetermined distance on a curve determined beforehand in accordance with the size of the object 2, and scans the sliding surface 2a of the object 2. Thereby, the total surface of the object 2 is scanned for detecting the defects.

Figure 4:
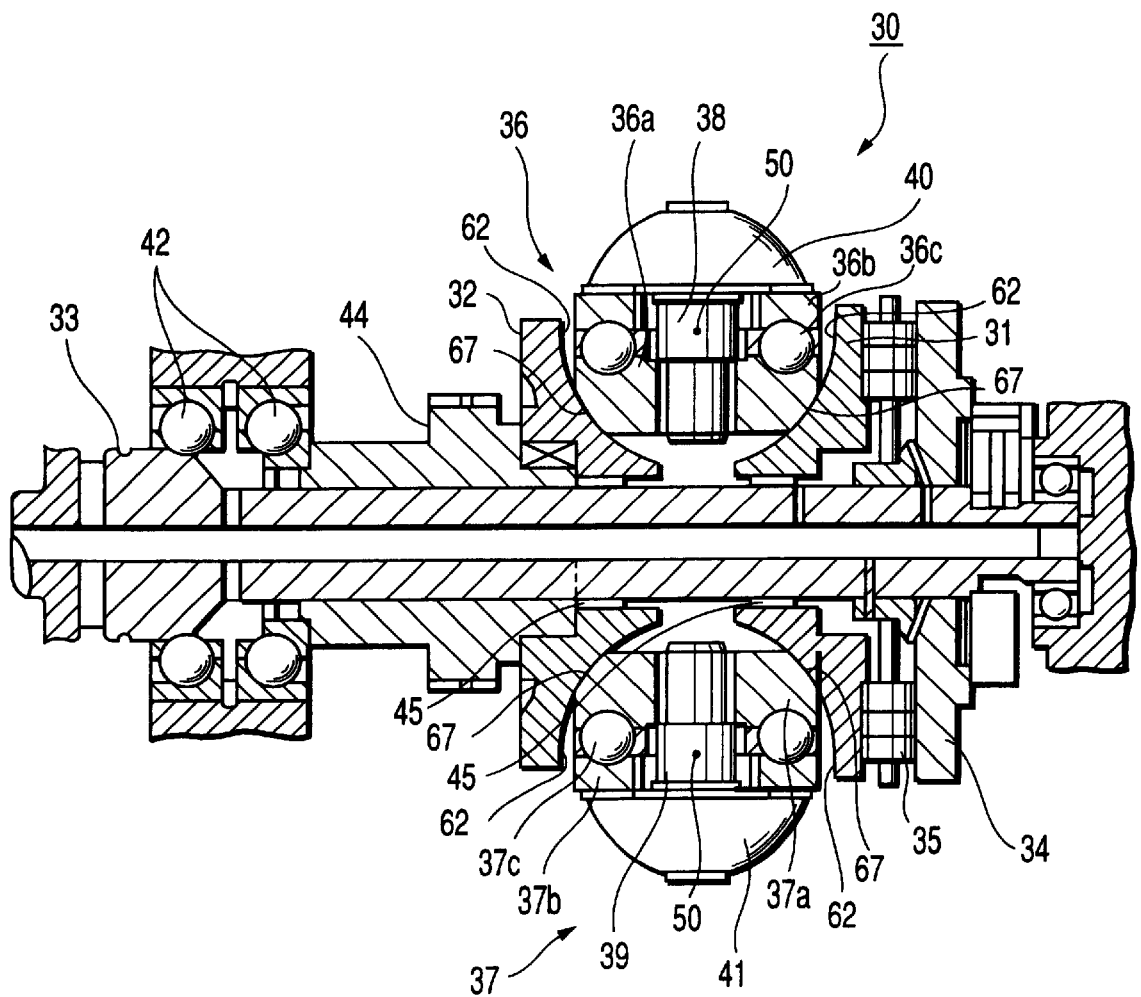
FIG. 4 is a sectional view of a CVT.

A toroidal CVT apparatus 30 will next be described with reference to FIG. 4.

The apparatus has a structure in which an input disk 31 and output disk 32 are disposed opposite to each other on the same shaft in a housing (not shown). An input shaft 33 is passed through a axis center portion of the toroidal transmission including the input disk 31 and output disk 32. A loading cam 34 is disposed on one end of the input shaft 33. Moreover, the loading cam 34 transmits a power (turning force) of the input shaft 33 to the input disk 31 via a cam roller 35 in the structure.

The input disk 31 and output disk 32 have substantially the same shape, are symmetrically disposed, and are formed on the traction surface so that the opposite surfaces of the disks cooperate to form a substantially semicircular shape as viewed in a axial section. Moreover, a pair of power roller bearing 36 and power roller bearing 37 for transmitting operation are disposed in contact with the input disk 31 and output disk 32 in toroidal cavities formed by the traction surfaces 62 of the input disk 31 and output disk 32 in the structure.

Additionally, the power roller bearing 36 includes an inner ring 36a, outer ring 36b and a plurality of rolling members (steel balls) 36c of the power roller bearing which rolls/runs on the traction surfaces 62 of the input disk 31 and output disk 32. Similarly, the other power roller bearing 37 includes a power roller inner ring 37a, outer ring 37b and a plurality of rolling members (steel balls) 37c which roll/run on the traction surfaces 62 of the input disk 31 and output disk 32.

That is, the power roller bearing inner rings 36a, 37a also serve as the rolling members of the power roller bearings 36, 37, respectively. One power roller bearing inner ring 36a is rotatably attached to a trunnion 40 via a pivot 38, the outer ring 36b and the plurality of rolling members 36c, and supported so that the ring can be tilted/rotated centering on a pivot shaft 50 as a center of the traction surfaces of the input disk 31 and output disk 32.

The other power roller bearing inner ring 37a is rotatably attached to a trunnion 41 via a pivot 39, the outer ring 37b and the plurality of rolling members 37c, and supported so that the ring can be tilted/rotated centering on the pivot shaft 50 as the center of the traction surfaces of the input disk 31 and output disk 32. Furthermore, a lubricant having a large viscosity friction resistance is supplied to mutual contact surfaces of the input and output disks 31, 32 and power roller bearing inner rings 36a, 37a. The power inputted into the input disk 31 is transmitted to the output disk 32 via a lubricant film and power roller bearing inner rings 36a, 37a in this lubricated state.

Additionally, the input disk 31 and output disk 32 are independent of the input shaft 33 via needles 45 (that is, the disks are not directly influenced by the power of the rotation shaft 33). An output shaft 44 disposed in parallel with the input shaft 33 and rotatably supported by the housing (not shown) via angular bearings 42 is disposed on the output disk 32.

The power of the input shaft 33 is transmitted to the loading cam 34 in the toroidal continuously variable transmission 30. Moreover, when the loading cam 34 rotates by the transmitted power, the power by the rotation is transmitted to the input disk 31 via the cam roller 35, and the input disk 31 rotates. Furthermore, the power generated by the rotation of the input disk 31 is transmitted to the output disk 32 via the power roller bearing inner rings 36a, 37a. Additionally, the output disk 32 rotates integrally with the output shaft 44.

During the transmission, the trunnions 40 and 41 are moved in a pivot shaft 50 direction by a micro distance. That is, by the axial movement of the trunnions 40 and 41, the intersections of the rotation shafts of the power roller bearing inner rings 36a, 37a and the shafts of the input disk 31 and output disk 32 slightly deviate. Then, a balance between rotation peripheral speeds of the power roller bearing inner rings 36a, 37a and input disk 31 is destroyed, and both the power roller bearing inner rings 36a, 37a are tilted/rotated around the pivot shaft 50 by a component force of a rotating/driving force of the input disk 31.

Therefore, both the power roller bearing inner rings 36a, 37a are tilted/rolled on curved surfaces of the input disk 31 and output disk 32, a speed ratio changes as a result, and deceleration or acceleration is performed.

A limit of an angle of incidence of an ultrasonic wave in the present invention will next be described. That is, an angle wave method in which the angle of incidence exceeds 30° will be described.

On entering the member to be inspected containing iron, steel at an angle of incidence $i_L$, the ultrasonic wave is divided into transverse and longitudinal waves, and an angle of refraction $\theta_L$ of the longitudinal wave is larger than an angle of refraction $\theta_S$ of the transverse wave. When water and iron conducts the ultrasonic wave, the relation between the angle of incidence and angle of refraction only with respect to the transverse wave is a relation represented by the following equations (7) and (8).

$$\sin \theta_S = V_2/V_1 \cdot \sin (i_L) \quad (7)$$

$$\sin \theta_S = 3230/1500 \cdot \sin (i_L) \quad (8)$$

Additionally, $\theta_S < 90°$ $V_1$: Sonic speed of 1500 m/second in water
$V_2$: Sonic speed of 3230 m/second in iron The probe 3 for ultrasonic inspection serves as both a transmitter and receiver, and a received signal (flaw signal) returns along a reverse path (tracks backwards along the same path as that of transmission). An intensity of echo returns to water from iron, steel, but the return signal may be either the transverse wave or the longitudinal wave, and both the transverse and longitudinal waves may return.

When the angle of incidence $i_L$ is not less than a certain value, the angle of refraction in iron, steel is not less than 90°, and the flaw signal only runs on the surface or is reflected by the surface and does not return to the probe 3 for the ultrasonic inspection.

When the angle of refraction $\theta_L$ of the longitudinal wave>the angle of refraction $\theta_S$ of the transverse wave with respect to the angle of incidence $i_L$ as described above, and additionally either $\theta_L$ or $\theta_S$ may return, the limit of the angle of incidence for returning $\theta_S$ may be considered.

The limit of the angle of incidence is theoretically about 28° from the above equations (7) and (8) in which $\theta_S$: 90° is assumed. However, in actual, the sonic wave is issued with a certain degree of width, and the flaw can sufficiently be detected at 30°.

Additionally, in general, a case in which the angle of refraction $\theta_S$ of the transverse wave is 90° is called a surface wave method. However, in actual, the sonic wave is oscillated from a vibrator with a certain degree of width (spread). Therefore, a case in which the angle of incidence $i_L$ is in a range of 26° to 30° is defined as the "surface wave method" in the present invention. Moreover, in general, a case in which the angle of incidence is 0° is called a normal wave method. However, in actual, the ultrasonic wave oscillated from the focus type probe is incident upon an optical axis with a certain degree of angle. Therefore, a case in which the angle of incidence $i_L$ is in a range of 0° to 5° is defined as the "normal wave method" in the present invention. Furthermore, a case in which the angle of incidence $i_L$ is in a range of 6 to 25° is defined as an "angle wave method" in the present invention.

(Embodiment 1)

A method of detecting the defect in the disk of the toroidal CVT and evaluating the detected defect will next be described as Embodiment 1.

Inspection conditions of Embodiment 1 will next be described.

Inspection methods: Surface wave method, angle wave method, normal wave method

Probe: Focus type probe (focus distance: position of 30 to 40 mm in water)

Frequency: 10 to 25 MHz

Table 3 shows results of evaluation as to whether or not the defect with a square root length of 0.05 mm performed can be detected. The evaluation was performed, while the angle of incidence of the ultrasonic wave was changed. When the inspection method comprised: scanning the disk for the flaw by each angle of incidence; and detecting the defect, the position and size of the defect were actually specified from the surface of the disk by run-in grinding, a relation between detection intensity and depth was derived, and the defect was evaluated based on the relation.

In Table 3, when an inclusion having a square root length of 0.05 mm can be detected in each position of the angle of incidence, a circle (○) is indicated. When the inclusion having the square root length of 0.05 mm cannot be detected, a cross (x) is displayed. Furthermore, when the defect can be detected, a position having a highest intensity of reflected echo is indicated with a double circle (◎) is indicated. Additionally, when the defect can be detected, a position having unclear echo is indicated with a triangle (Δ). The frequency of the used probe was in a range of 10 MHz to 25 MHz. Moreover, the distance from the sliding surface was calculated using the maximum shear stress depth $Z_0$ in test conditions of the example described later as a reference ($Z_0$ is about 1 mm in Example 1).

As shown in Table 3, when the depth is less than $Z_0 \times 2$ (mm), the position is in a dead band of a surface layer, and therefore a small defect having a square root length less than 0.05 mm cannot be detected at an angle of incidence of 0° (perpendicular wave). Conversely, when the depth is less than $Z_0 \times 2$ (mm), the defect can be detected at an angle of incidence of 17° (oblique angle) and an angle of incidence of 30° (surface wave). It has also been found that the attenuation of the ultrasonic wave is remarkable in a depth region exceeding $Z_0 \times 2$ (mm) and it is therefore difficult to detect the defect. Moreover, a difference is recognized in the depth having the maximum reflected echo intensity in accordance with the selected angle of incidence, the surface wave method is best for the vicinity of the surface, and the angle wave method is best for a slightly deep region. Therefore, it is necessary to select incidence conditions of the ultrasonic wave in the surface to be inspected in accordance with the depth of the disk to be inspected.

According to Embodiment 1 described above, when the perpendicular wave method is combined with the oblique angle or surface wave method, it is possible to detect a large defect having a square root length of 0.05 mm or more existing in the portion having a depth of $Z_0 \times 2$ (mm) from the surface.

(Embodiment 2)

The traction surface of the CVT disk was subjected to the ultrasonic inspection similarly as Example 1, the disks in which the square root lengths of the detected defects are in ranges of 0.05 mm to 0.07 mm and 0.10 mm to 0.12 mm were taken out, further test pieces were classified by the depth from the sliding surface, and a durability test was performed. Additionally, the depth in which the defect was present was sorted out with the multiple of the maximum shear stress generated position $Z_0$ in the following durable condition.

(Test Conditions)

Rotation speed of input: 4000 rpm

Input torque: 450 N·m (torque of a maximum deceleration time)

Used oil: synthetic lubricant (traction oil)

Oil temperature: 100° C.

Figure 5:
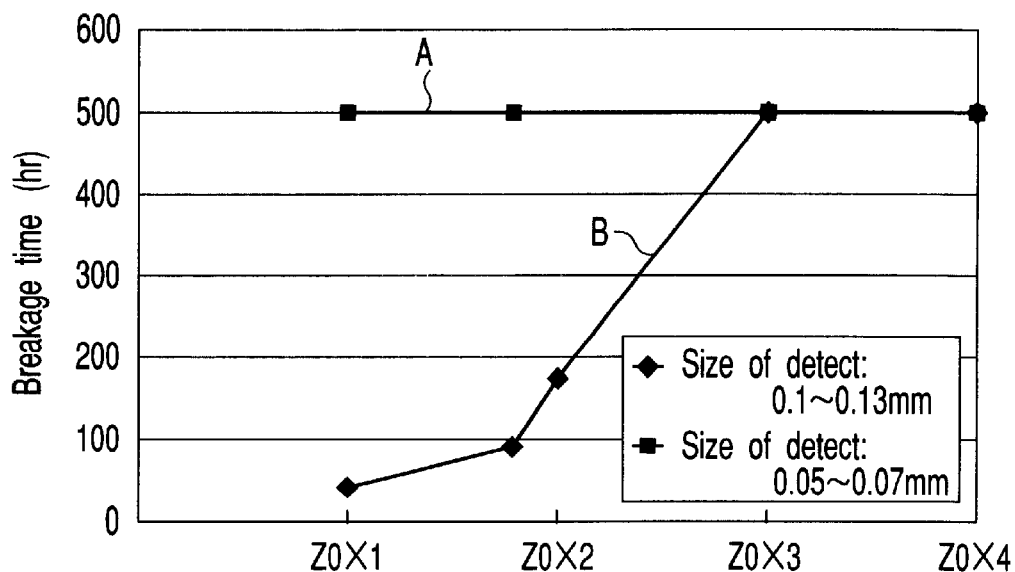
FIG. 5 is a characteristic graph showing an evaluation test result.

The test results are shown in FIG. 5 and Table 1. FIG. 5 is a characteristic graph in which the abscissa indicates the position of the defect from the surface, the ordinate indicates the breakage time of the member in the durability test, and a result of check concerning the influence of the size and position of the defect onto a breakage time (life) is shown. In the drawing, a characteristic line "A" shows the result of check of the breakage time with respect to the member to be inspected in which the defects each having the square root length in a range of 0.05 to 0.07 mm exist in depth positions once, twice, three times, four times the maximum shear stress depth $Z_0$. A characteristic line "B" shows the result of check of the breakage time with respect to the member to be inspected in which the defects each having the square root length in a range of 0.10 to 0.13 mm exist in the depth positions once, nearly twice, a little over twice, three times, four times the maximum shear stress depth $Z_0$. As apparent from the drawing, the defect (small defect) having a square root length of 0.05 to 0.07 mm does not influence the breakage life regardless of the depth position. However, when the defect (large defect) having a square root length of 0.10 to 0.13 mm is positioned in the depth twice the maximum shear stress depth $Z_0$, the breakage life is remarkably short.

Moreover, as shown in Table 1, the inspected members No. 1 to No. 3 in which the depth position with the defects existing therein is within $Z_0 \times 2$ have large defects each having the square root length of 0.10 mm or more. It has been found that the members break in short times such as 40 hours, 90 hours, and 175 hours. On the other hand, even for the inspected members No. 4 and No. 5 having large defects each having the square root length of 0.10 mm or more, when the depth position with the defects existing therein exceeds $Z_0 \times 2$ and is $Z_0 \times 3$ or more, the members do not break even exceeding 500 hours. Moreover, even when the depth position with the defects existing therein is within $Z_0 \times 2$, the inspected members (No. 6 and No. 7) including the defects each having the square root length of 0.05 mm to 0.7 mm do not break even exceeding 500 hours.

Therefore, to prevent the CVT member undergoing a high load from breaking, it is essential not to include the nonmetal inclusion with a square root length of 0.10 mm or more in a depth range from the surface, which is twice the maximum shear stress depth $Z_0$.

Subsequently, the CVT disk was subjected to the ultrasonic flaw detection/inspection similarly as described above, the disks in which the square root lengths of the detected defects were in a range of 0.05 mm to 0.07 mm were selected, further the test pieces were classified by the depth from the sliding surface, and a rolling fatigue life of the disk was obtained in the above-described test condition. Additionally, the number of test pieces was set to n=20 for each depth condition, and L10 life of the peeled disk was obtained.

Figure 6:
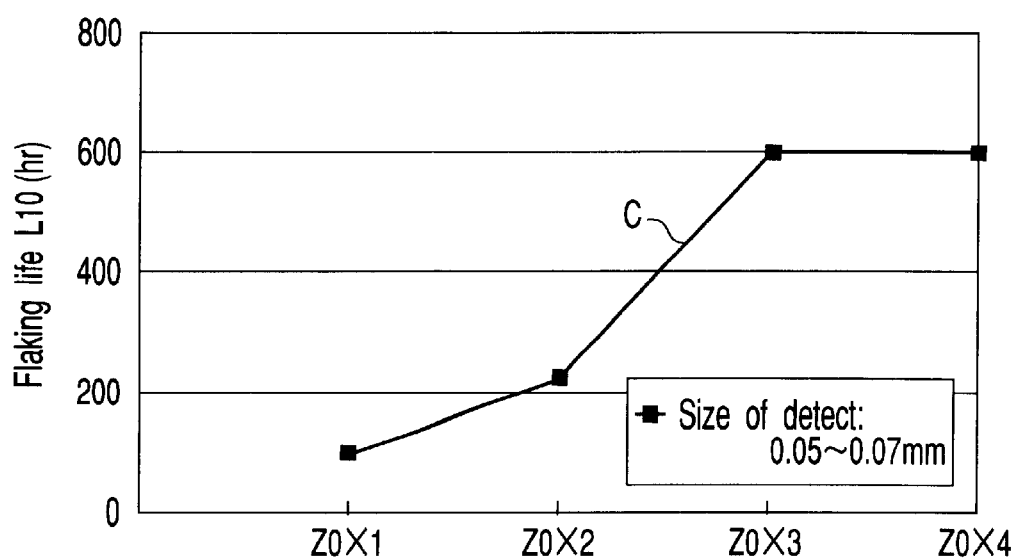
FIG. 6 is a characteristic graph showing the evaluation test result.

The life evaluation results are shown in FIG. 6 and Table 2. FIG. 6 is a characteristic graph in which the abscissa indicates the position of the defect from the surface, the ordinate indicates a flaking life L10 (time) of the member in an L10 life test, and a result of check concerning the influence of the position of the defect having the square root length of 0.05 to 0.07 mm onto the L10 life is shown. In the drawing, a characteristic line C is obtained by plotting and connecting the results of the check of the L10 life with respect to the inspected member in which the defects each having the square root length of 0.05 to 0.07 mm exist in depth positions once, twice, three times, four times the maximum shear stress depth $Z_0$. As apparent from the drawing, when the defect having the square root length of 0.05 to 0.07 mm is positioned in the depth within twice the maximum shear stress depth $Z_0$, the L10 life remarkably becomes short. This result was obtained. Additionally, it has been confirmed that the defect with the same size is substantially harmless for a fatigue flaking strength with a depth three or more times the maximum shear stress depth $Z_0$ (the flaking does not occur in 600 hours)

Moreover, even with a small defect which does not result in breakage and has a square root length of 0.05 to 0.07 mm, for inspected members No. 8 and No. 9 in which the defect exists within twice the maximum shear stress depth $Z_0$, the L10 lives of the members are 100 hours, 230 hours and the members have short lives (see Table 2). On the other hand, even when inspected members No. 10 and No. 11 includes defects each having a square root length of 0.05 mm or more, but when their depth positions with the defects existing therein exceeds $Z_0 \times 2$ and are not less than $Z_0 \times 3$, the members have nearly tripled L10 lives (600 hours or more). This has been found (see Table 2).

Therefore, to prevent short life flaking, it is essential not to include the defect having a square root length of 0.05 mm or more (particularly the nonmetal inclusion) within a depth range from the traction surface of the toroidal CVT disk, which is twice the maximum shear stress depth ($Z_0$).

TABLE 1

| No. | Steel type | Square root length (mm) | Position of defect (mm) | Breakage time (Hr) |
|---|---|---|---|---|
| 1 | SCM435 | 0.1–0.13 | $Z_0 \times 1$ | 40 |
| 2 | SCM420 | 0.1–0.13 | $Z_0 \times 1.8$ | 90 |
| 3 | SCM435 | 0.1–0.13 | $Z_0 \times 2$ | 175 |
| 4 | SCM435 | 0.1–0.13 | $Z_0 \times 3$ | 500 or more (does not break) |
| 5 | SCM420 | 0.1–0.13 | $Z_0 \times 4$ | 500 or more |
| 6 | SCM435 | 0.05–0.07 | $Z_0 \times 1$ | (does not break) |
| 7 | SCM420 | 0.05–0.07 | $Z_0 \times 1.8$ | 500 or more (does not break) |

TABLE 2

| No. | Steel type | Square root length (mm) | Position of defect (mm) | L10 life time (Hr) |
|---|---|---|---|---|
| 8 | SCM435 | 0.05–0.07 | $Z_0 \times 1$ | 100 |
| 9 | SCM420 | 0.05–0.07 | $Z_0 \times 2$ | 230 |
| 10 | SCM435 | 0.05–0.07 | $Z_0 \times 3$ | 600 or more |
| 11 | SCM420 | 0.05–0.07 | $Z_0 \times 4$ | 600 or more |

TABLE 3

| Depth from surface (mm) | Angle of incidence | | |
|---|---|---|---|
| | 0° (normal wave method) | 17° (angle wave method) | 30° (surface wave method) |
| $Z_0 \times 0$ | x | ○ | ⊙ |
| $Z_0 \times 1$ | x | ⊙ | ○ |
| $Z_0 \times 2$ | ○ | Δ | Δ |
| $Z_0 \times 3$ | ○ | x | x |
| $Z_0 \times 4$ | ○ | x | x |
| $Z_0 \times 5$ | ○ | x | x |

A method of inspecting a portion in which the stress builds up other than the traction surfaces of the input/output disk and power roller bearing inner ring of the toroidal CVT will next be described as Examples 3, 4 of the present invention with reference to FIGS. 7, 8, 15 to 18 and Tables 4, 5. Additionally, materials dissolved from different material charges were used to manufacture the input/output disks 31, 32 and power roller bearing inner rings 36a, 37a. After completion and before assembly, the angle wave method and normal wave method were used to check whether or not the large nonmetal inclusion having a square root length of 0.20 mm or more exists in the portions shown by diagonal lines in FIGS. 7, 8.

A steel material of JIS SCM435 was used in the materials of the input disk 31 and power roller bearing inner rings 36a, 37a. The steel material was subjected to a carbonitriding treatment so that the total concentration of carbon and nitrogen of the surface was in a range of 0.9 to 1.2%, and subsequently subjected to hardening/tempering, and the surface was finished/processed. The hardness of the finished/processed surface was in a range of 720 to 780 in terms of Vickers hardness Hv. Additionally, with case-hardened steel, a surface hardening treatment may be performed as described above. With the similar hardness, for example, JIS SCM420, SCM440, SCR420, and the like may be used. Moreover, even when a carburization treatment is performed instead of the above-described carbonitriding treatment, the similar result is obtained with respect to a crack life. Additionally, similar materials are also used in output disk 32 and power roller bearing outer rings 36b, 37b.

Figure 15:
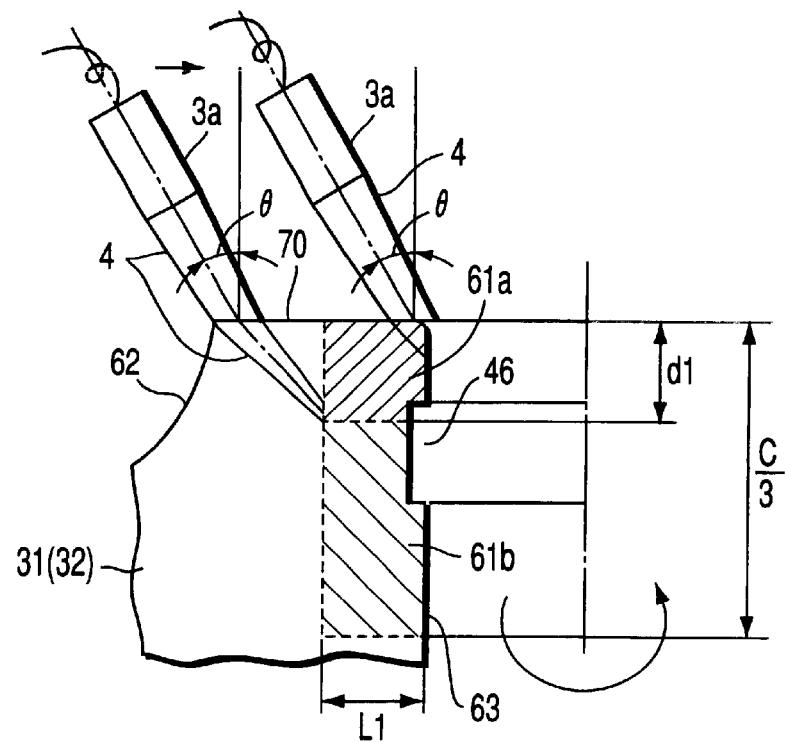
FIG. 15 is a schematic view showing an angle wave method for use in inspecting a major surface layer portion (first region) of the input disk.
Figure 16:
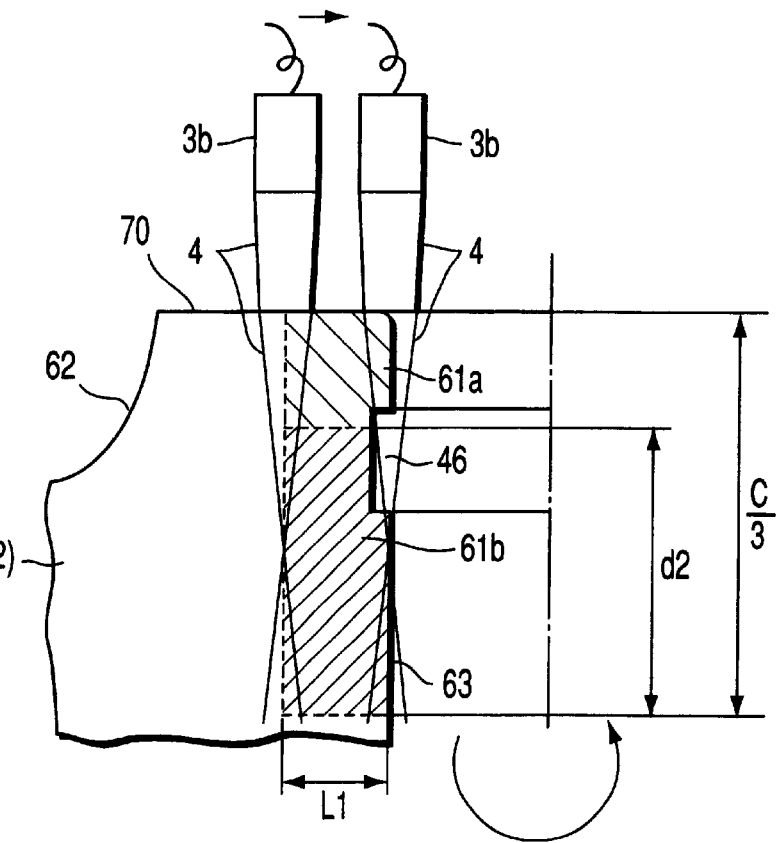
FIG. 16 is a schematic view showing a normal wave method for use in inspecting a quasi surface layer portion (second region) of the input disk.
Figure 17:
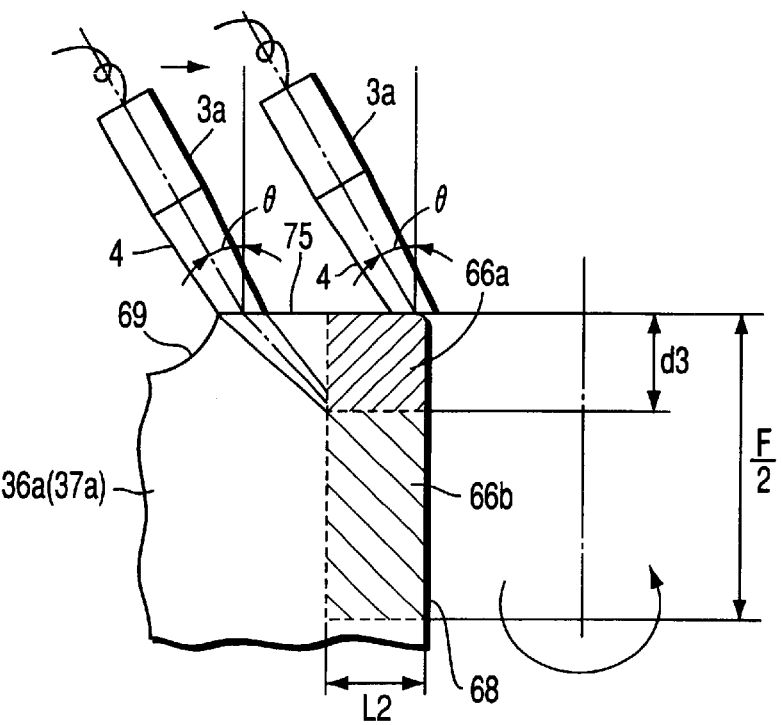
FIG. 17 is a schematic view showing the angle wave method for use in inspecting the major surface layer portion (first region) of the power roller bearing inner ring.
Figure 18:
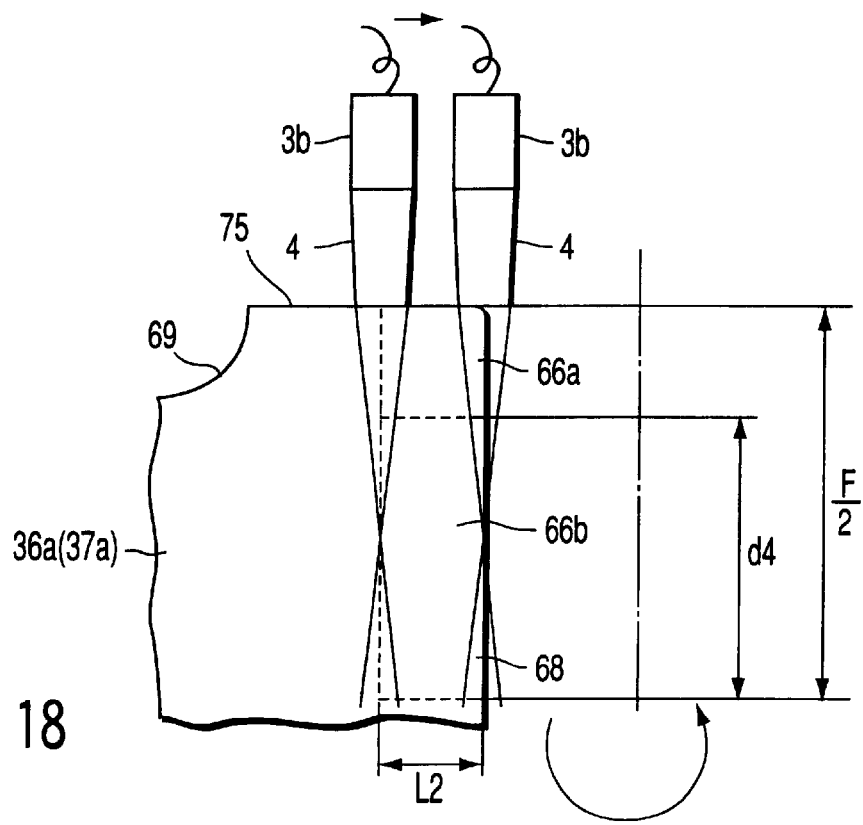
FIG. 18 is a schematic view showing the normal wave method for use in inspecting the quasi surface layer portion (second region) of the power roller bearing inner ring.
Figure 19:
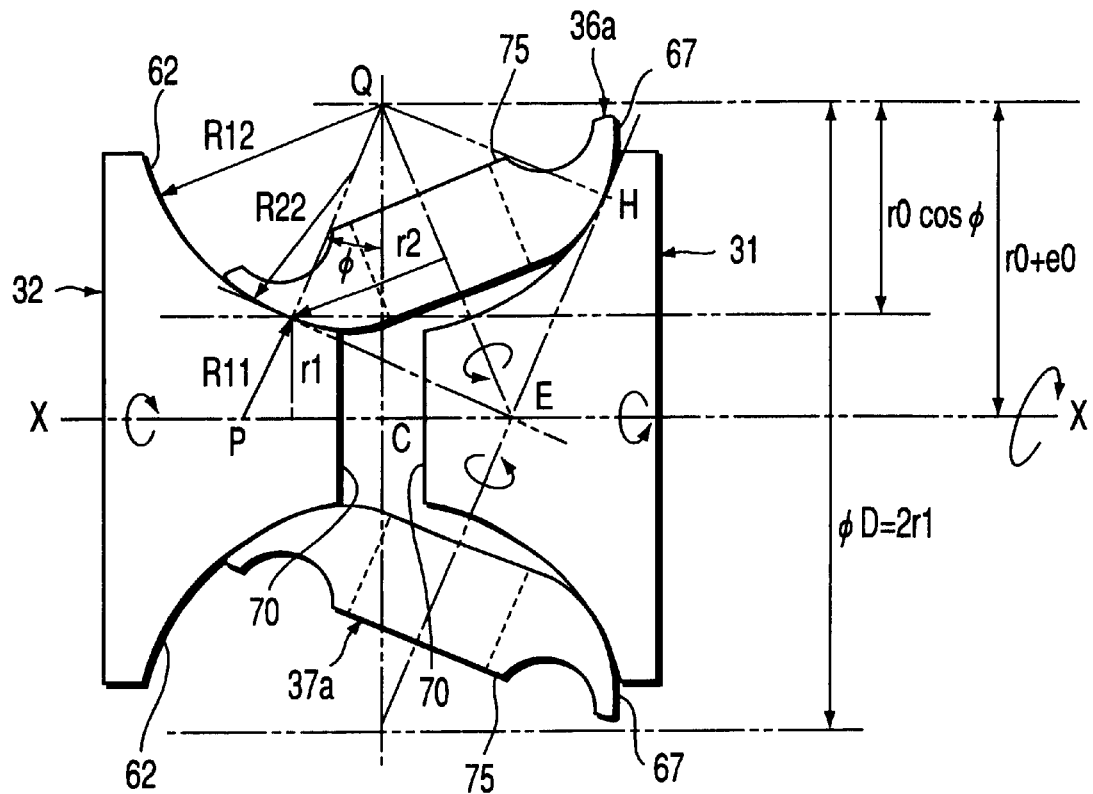
FIG. 19 is a schematic view showing the input/output disk and power roller bearing member in a contact state and Hertz's elastic contact theory.
Figure 20:
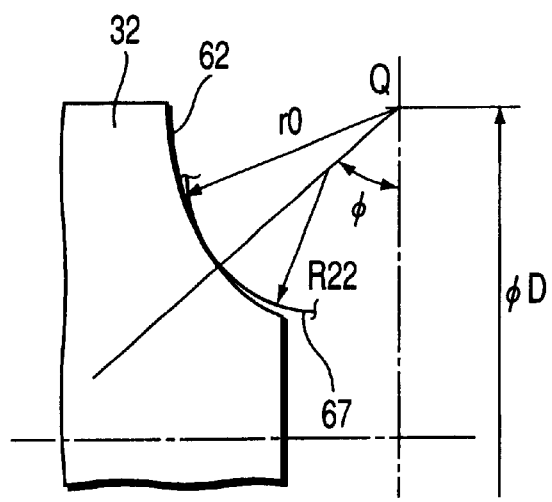
FIG. 20 is an enlarged schematic view showing a part of FIG. 19.

A common evaluation method of inspecting the portion in which the stress rises other than the traction surfaces of the input/output disk and power roller bearing inner ring comprised: using the apparatus shown in FIGS. 1 to 3 to subject the portion to the ultrasonic flaw detection. In the input disk 31, as shown in FIG. 15, the depth of 3 mm (inspection gate) from an end surface 70 was scanned at an angle of incidence of 28° (angle of refraction of 90°). In the power roller bearing inner ring 36a, as shown in FIG. 17, the depth of 3 mm (inspection gate) from an end surface 77 was scanned at an angle of incidence of 19° (angle of refraction of 45°) As shown in FIGS. 16, 18, the depth of 3 mm or more from the end surface was perpendicularly scanned at the angle of incidence of 0°. The probe was operated so as to obtain the above-described angle of incidence, and the size (width and length) and position of the defect were estimated/evaluated from information such as X-Y axis coordinate, R axis angle, height of defect echo, reflected range of echo, and beam exposure distance from the echo in automatic flaw detection.

(Embodiment 3)

A method of inspecting a surface layer portion 61 right under the inner peripheral surface/end surface of the disk 31 (32) will be described as Embodiment 3 with reference to FIGS. 15, 16 and Table 4.

Figure 7:
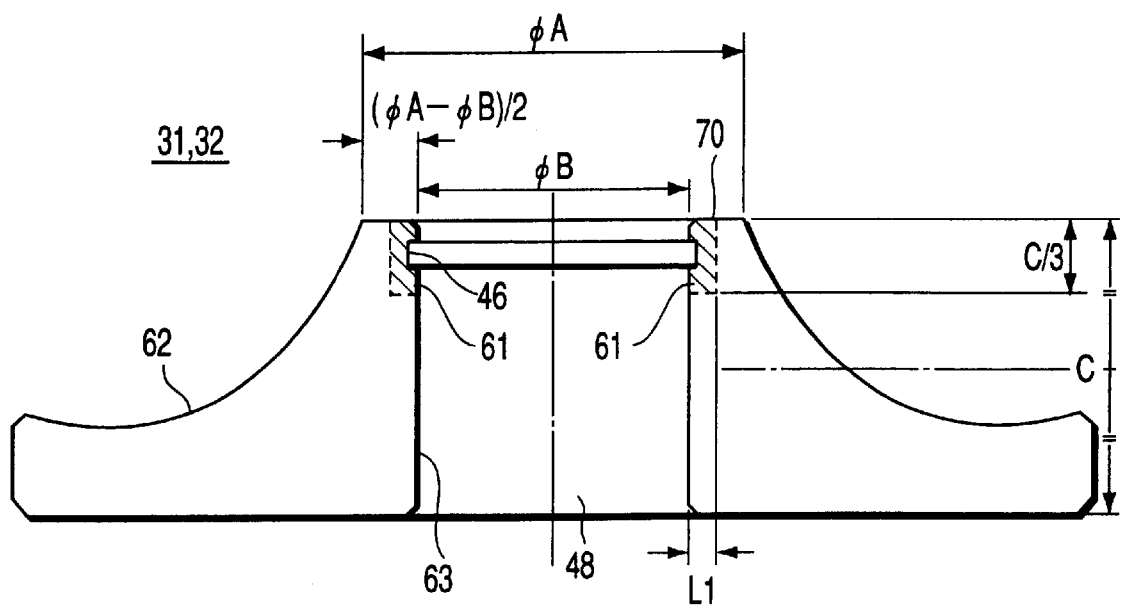
FIG. 7 is a sectional schematic view showing a portion to be inspected of an input/output disk.

As shown in FIG. 7, the inspection object portion 61 of the disk is assumed to be in a range of a depth L1 which is a half of the diametric length of the end surface 70 from an inner peripheral-surface 63 side (about the half of the end surface 70 (e.g., 6 mm), and a depth C/3 which is at least 1/3 of the axial length of the inner peripheral surface 63 from an end surface 70 side.

First, the disk 31 is immersed in water as the ultrasonic wave transmission medium, and the ultrasonic oscillation surface of the probe (not shown) is positioned with respect to the end surface 70 of the disk 31 so that the angle of incidence θ is 28° (the angle of refraction is 90°). It is confirmed that the probe is correctly positioned in a flaw detection start position with the surface wave incident thereupon. Thereafter, the disk 31 is rotated around the shaft at a predetermined rotation speed. Moreover, the ultrasonic wave is oscillated toward the end surface 70 of the disk 31, and the surface wave probe (not shown) is moved in parallel with the radial direction of the disk 31 toward an inner peripheral side from an outer peripheral side. Thereby, the end surface 70 is scanned in a range of width L1 from the inner peripheral surface 63 of the disk 31.

Subsequently, the ultrasonic oscillation surface of a probe 3a attached to the arm 23 is positioned with respect to the end surface 70 of the disk 31 so as to obtain the angle of incidence θ of 19° (angle of refraction of 45°). Subsequently, the disk 31 is rotated around the shaft at the predetermined rotation speed, the ultrasonic wave is oscillated toward the end surface 70 of the disk 31, and the probe 3a is moved in parallel with the radius direction of the disk 31 toward the inner peripheral side from the outer peripheral side.

As shown in FIG. 15, ultrasonic waves 4 are incident upon the rotating disk 31 at the angle of incidence of 19° (θ) from the end surface 70, and the angle beam probe 3a is moved in parallel with the end surface 70 toward the right from the left of the drawing. Where an incidence portion of the ultrasonic wave 4 reaches a corner edge of the end surface 70, the parallel movement of the angle beam probe 3a is stopped. Thereby, a first portion 61a is scanned in a range of a depth dl (e.g., 2 to 3 mm) from the end surface 70 and a depth L1 from the inner peripheral surface 63 (a half of width W of the end surface 70 (e.g., 6 to 8 mm)).

Subsequently, the angle beam probe 3a is detached from the arm 23, and replaced with a normal beam probe 3b. The normal beam probe 3b is positioned with respect to the end surface 70 of the disk 31. After confirming that the normal beam probe 3b is correctly positioned in the flaw detection start position, the disk 31 is rotated around the shaft at the predetermined rotation speed, the ultrasonic wave is oscillated toward the end surface 70 of the disk 31 and the normal beam probe 3b is moved in parallel with the radius direction of the disk 31 toward the inner peripheral side from the outer peripheral side.

As shown in FIG. 16, the ultrasonic waves 4 are incident upon the rotating disk 31 at the angle of incidence of 0° from the end surface 70, and the normal beam probe 3b is moved in parallel with the end surface 70 toward the right from the left of the drawing. Where the incidence portion of the ultrasonic wave 4 reaches the corner edge of the end surface 70, the parallel movement of the normal beam probe 3b is stopped. Thereby, a second portion 61b is scanned in a range of a depth d1+d2 (=C/3) from the end surface 70 and the depth L1 from the inner peripheral surface 63 (the half of width W of the end surface 70 (e.g., 6 to 8 mm)).

Prior to the evaluation of the crack life (L10 life), the size and position of the defect were estimated as follows. The disk from which some defect echoes could be obtained was cut, the cut surface was observed in detail with a microscope, and thereby a relation (calibration) between the size (width and length) and depth position from the surface of the large nonmetal inclusion and the ultrasonic echo intensity was grasped. The calibration and measured defect echo were used to estimate the size and position of the defect which would be inside the member.

Table 4 shows the position and size of the defect (large nonmetal inclusion) detected beforehand in the input disk used in crack life evaluation. Additionally, since a larger load was applied to the input disk than to the output disk (used in the strict stress condition), the input disk was representatively tested. These test specimens were used to perform a simulation durability test of the apparatus with the toroidal CVT mounted thereon, and it was evaluated whether or not any crack was generated. Additionally, the disk and power roller bearing inner ring (other members) for use in materials other than the test materials used in the durability test underwent the ultrasonic inspection beforehand. The members were confirmed that the amount of large nonmetal inclusions was smaller than that of test specimens, and subsequently the members were used.

TABLE 4

| | Detected position of large inclusion | | Size of large inclusion | | | |
|---|---|---|---|---|---|---|
| Sample No. | Distance from end surface [depth direction] (mm) | Distance from inner peripheral surface (mm) | Width (mm) | Length (mm) | Square root length (mm) | Fatigue crack breakage time of input disk (Hr) |
| Sample 1 | C/20 | W/8 | 0.20 | 0.20 | 0.20 | 100 or more |
| Sample 2 | C/11.4 | W/2 | 0.12 | 0.18 | 0.15 | 100 or more |
| Sample 3 | C/8 | W/4 | 0.10 | 0.35 | 0.19 | 100 or more |
| Sample 4 | C/5 | W/4.6 | 0.08 | 0.35 | 0.17 | 100 or more |
| Sample 5-1 | C/4 | W/2 | 0.07 | 0.50 | 0.19 | 100 or more |
| Sample 5-2 | C/3 | W/2 | 0.18 | 0.18 | 0.18 | 100 or more |
| Sample 6 | C/2.7 | W/3.6 | 0.22 | 0.22 | 0.22 | 100 or more |
| Sample 7 | C/2.0 | W/5.3 | 0.20 | 0.40 | 0.28 | 100 or more |
| Sample 8 | C/16 | W/1.9 | 0.12 | 0.40 | 0.22 | 100 or more |
| Sample 9 | C/5.7 | W/1.8 | 0.25 | 0.30 | 0.27 | 100 or more |
| Sample 10 | C/4 | W/1.6 | 0.18 | 0.50 | 0.30 | 100 or more |
| Sample 11 | C/4 | W/2 | 0.20 | 0.25 | 0.22 | 60 |
| Sample 12 | C/10 | W/3.2 | 0.15 | 0.35 | 0.23 | 45 |

After the above-described treatment was performed, the surface of the disk was ground/processed, and used in the ultrasonic inspection.

Test conditions are as follows:
Rotation speed of input shaft; 4000 rpm
Input torque; 392 N·m (torque of maximum deceleration time)
Used oil; synthetic lubricant
Oil temperature; 100° C.

In the durability test, a time required until each input disk as the test material cracks was checked. As apparent from Table 4, even when the detected position of the defect is in a diagonal-line region of FIG. 7, but when the defect size is 0.20 mm or less in terms of the square root length, the crack has been found not to be generated even exceeding 100 hours (Samples 1 to 5-2).

Moreover, even when the large inclusion with a square root length exceeding 0.2 mm exists, but when the depth (distance) from the end surface 70 or the depth (distance) from the inner peripheral surface 63 is outside the diagonal-line region of FIG. 7, the crack has been found not to be generated even exceeding 100 hours (Samples 6 to 10). That is, in Table 4 and FIG. 7, the large inclusion with a square root length exceeding 0.20 mm is prevented from existing in the portion (diagonal-line region 61 of FIG. 7) with the distance of C/3 or less in the height direction from the end surface 75 of the disk and within the distance L1 (W/2) from the inner peripheral surface 63 of a through hole 48 in which a support shaft is to be inserted. Then, the disk attains a long life. Additionally, the above-described parameter C is a total height size of the disk, and a parameter W is a size defined by W=(A−B)/2 in which the outer diameter of a vertex portion of the disk is A and the diameter of the hole 48 is B.

On the other hand, when the depth (distance) from the end surface 70 or inner peripheral surface 63 was within the diagonal-line region 61 of FIG. 7, and when the large inclusion with the square root length exceeding 0.20 mm existed, some members cracked in 60 hours (Sample 11) and other members cracked in 45 hours (Sample 12). The start points of the cracks agreed with the positions in which the defects were found by the ultrasonic inspection.

Additionally, an inspection frequency is preferably 15 MHz or less, and the present inventors have confirmed that the similar results are obtained even with the use of the focus type probe with a frequency of 10 MHz.

(Embodiment 4)

A method of inspecting a surface layer portion 66 right under the inner peripheral surface/end surface of the CVT power roller bearing inner ring 36a (37a) will be described as Embodiment 4 with reference to FIGS. 17, 18 and Table 5.

Figure 8:
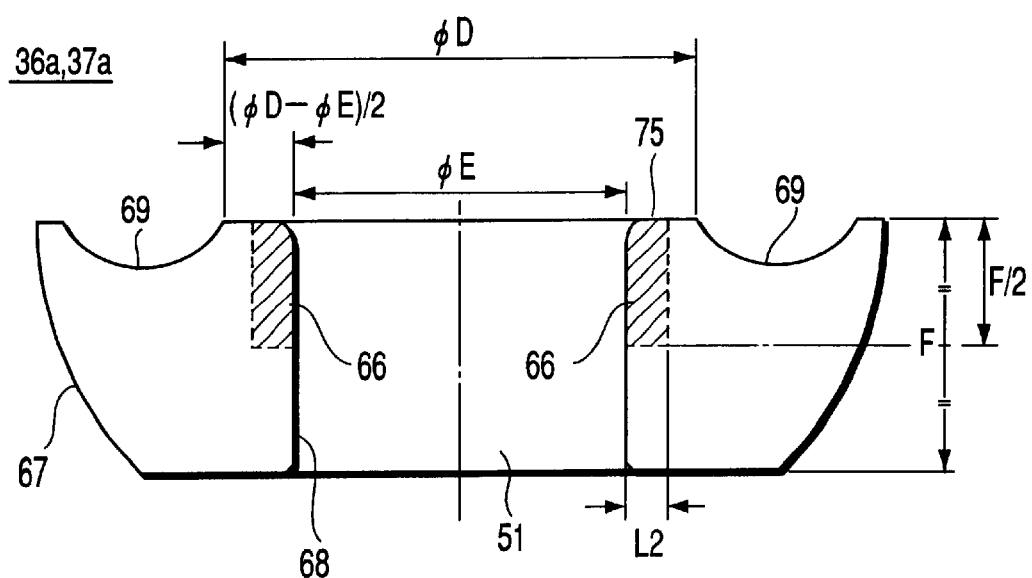
FIG. 8 is a sectional schematic view showing a portion to be inspected of a power roller bearing inner ring.
Figure 9:
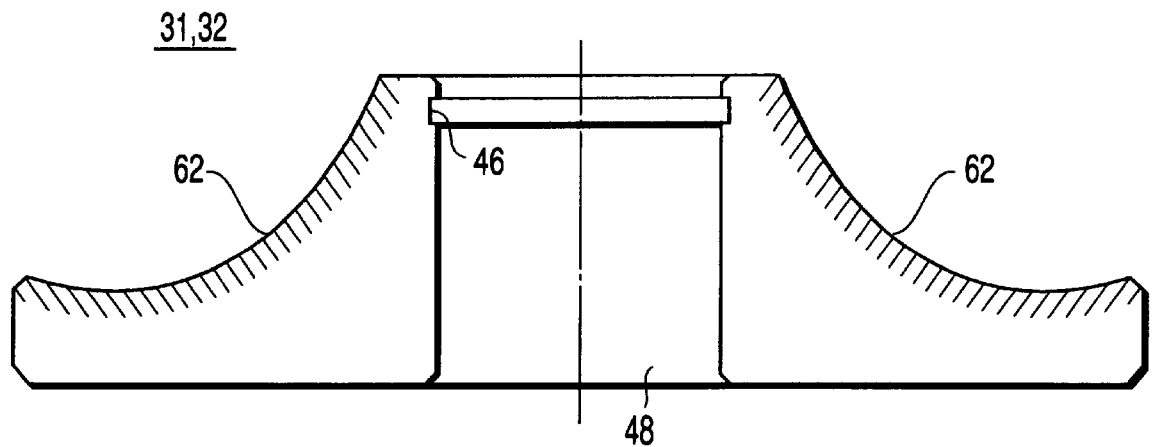
FIG. 9 is a sectional schematic view showing a portion to be inspected of a traction surface of the input/output disk.
Figure 10:
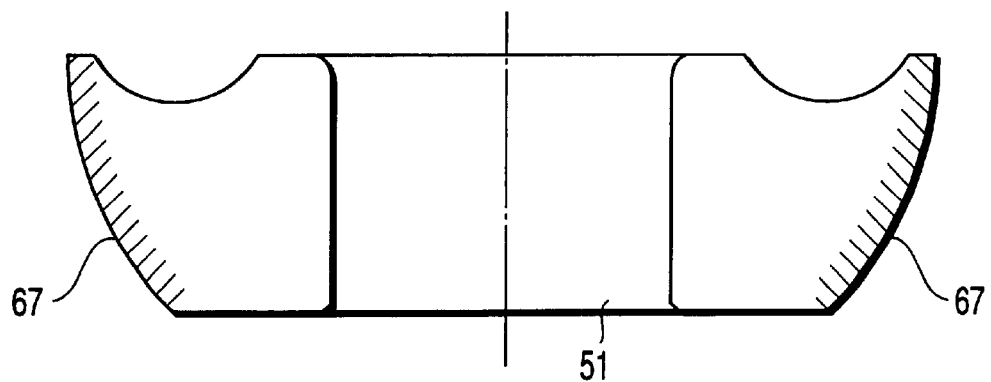
FIG. 10 is a sectional schematic view showing a portion to be inspected of the traction surface of the power roller bearing inner ring.
Figure 11:
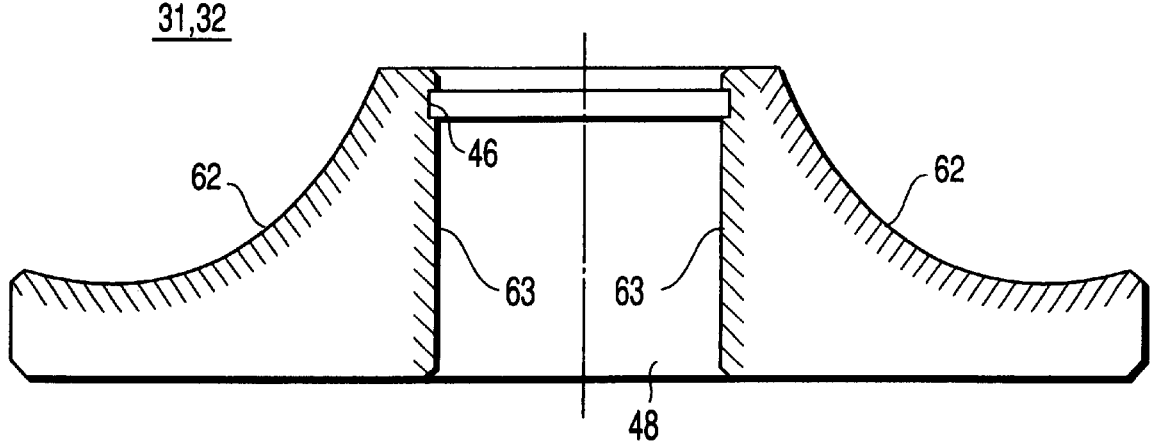
FIG. 11 is a sectional schematic view showing the portion to be inspected of the input/output disk.
Figure 12:
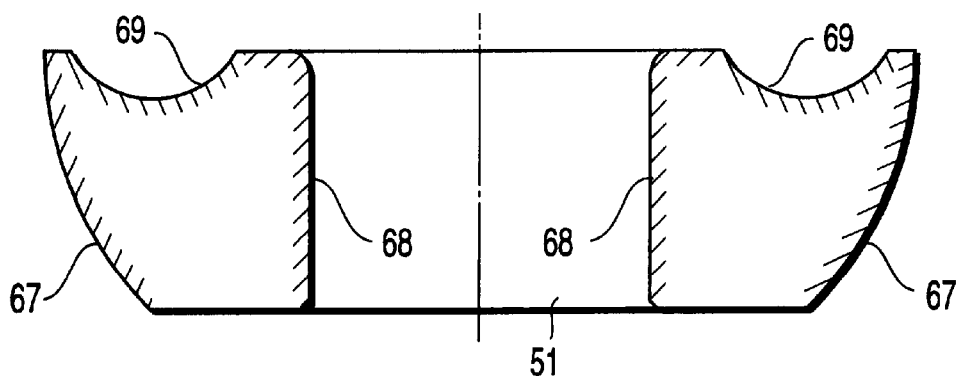
FIG. 12 is a sectional schematic view showing the portion to be inspected of the power roller bearing inner ring.
Figure 13:
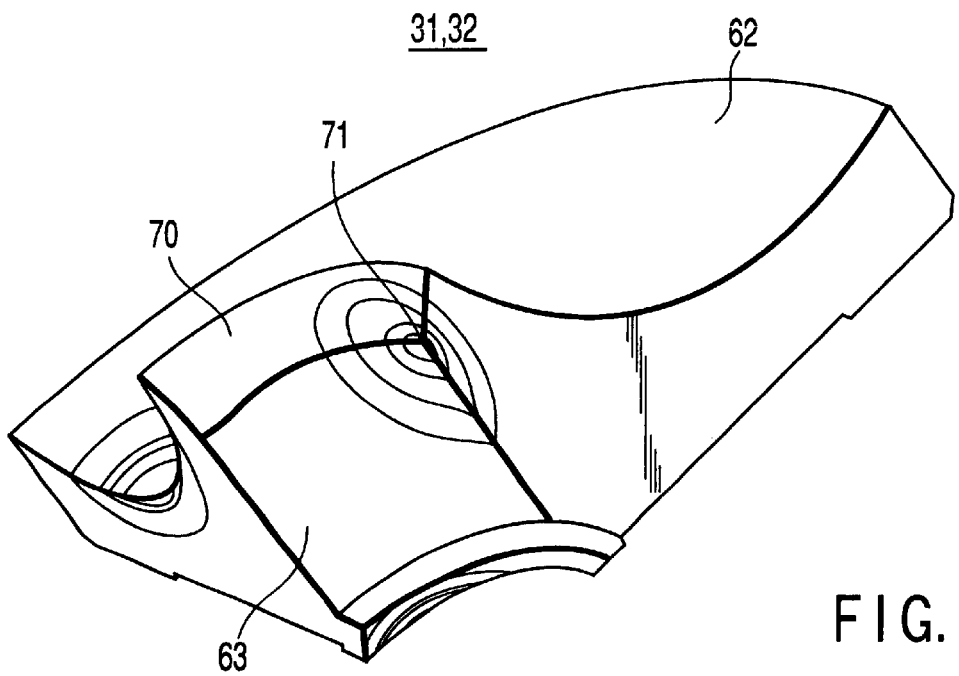
FIG. 13 is a three-dimensional image diagram showing the input/output disk whose stress has been analyzed by computer simulation using a finite element method (FEM).
Figure 14:
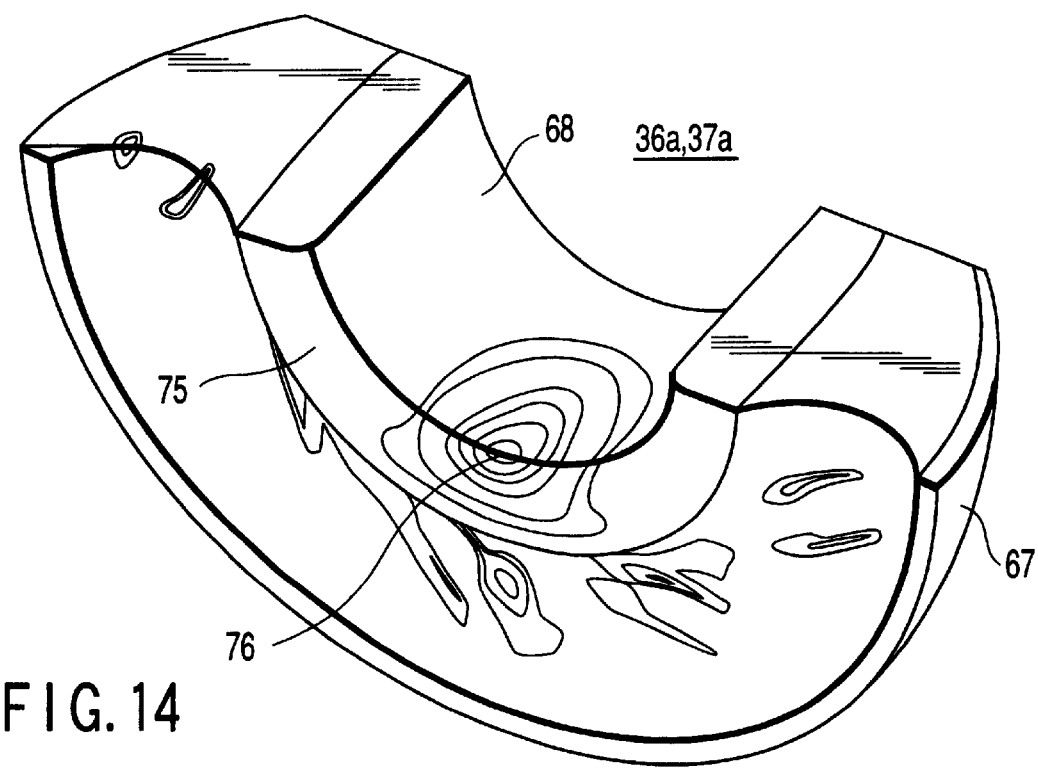
FIG. 14 is a three-dimensional image diagram showing the power roller bearing inner ring whose stress has been analyzed by the computer simulation using the finite element method (FEM).

As shown in FIG. 8, the inspection object portion 66 of the power roller bearing inner ring was assumed to be in a range of a depth L2 which was at least a half of the diametric length of the end surface from the inner peripheral surface side and a depth F/2 which was at least a half of the axial length of the inner peripheral surface from the end surface side.

First, the power roller bearing inner ring 36a is immersed in water as the ultrasonic wave transmission medium, and the ultrasonic oscillation surface of the probe 3a (not shown) is positioned with respect to the end surface 75 of the power roller bearing inner ring 36a so that the angle of incidence θ is 28° (the angle of refraction is 90°). It is confirmed that the probe is correctly positioned in the inspection start position with the surface wave incident thereupon. Thereafter, the power roller bearing inner ring 36a is rotated around the shaft at the predetermined rotation speed. Moreover, the ultrasonic wave is oscillated toward the end surface 75 of the power roller bearing inner ring 36a and the surface wave probe 3a (not shown) is moved in parallel with the radial direction of the power roller bearing inner ring 36a toward the inner peripheral side from the outer peripheral side. Thereby, the end surface 75 is scanned in a range of width L2 from the inner peripheral surface 68 (the half of width G).

Subsequently, the ultrasonic oscillation surface of the probe 3a attached to the arm 23 is positioned with respect to the end surface 75 of the power roller bearing inner ring 36a so as to obtain the angle of incidence θ of 19° (angle of refraction of 45°). The probe 3a is positioned so that the angle beam is correctly incident upon the inspection start position. After confirming this, the power roller bearing inner ring 36a is rotated around the shaft at the predetermined rotation speed, the ultrasonic wave is oscillated toward the end surface 75, and the probe 3a is moved in parallel with the radius direction of the power roller bearing inner ring 36a toward the inner peripheral side from the outer peripheral side.

As shown in FIG. 17, the ultrasonic waves 4 are incident upon the rotating power roller bearing inner ring 36a at the angle of incidence of 19° from the end surface 75, and the angle beam probe 3a is moved in parallel with the end surface 75 toward the right from the left of the drawing. Where the incidence portion of the ultrasonic wave 4 reaches the corner edge of the end surface 75, the parallel movement of the angle wave method probe 3a is stopped. Thereby, a first portion 61a is scanned in a range of a depth d3 (e.g., 1 mm) from the end surface 75 and the depth L2 from the inner peripheral surface 68 (the half of width G of the end surface 75 (e.g., 6 mm)).

Subsequently, the angle beam probe 3a is detached from the arm 23, and replaced with the normal beam probe 3b. The probe 3b is positioned with respect to the end surface 75 of the power roller bearing inner ring 36a. After confirming that the probe 3b is correctly positioned in the inspection start position, the power roller bearing inner ring 36a is rotated around the shaft at the predetermined rotation speed. The ultrasonic wave is oscillated toward the end surface 75 of the power roller bearing inner ring 36a and the normal beam probe 3b is moved in parallel with the radius direction of the power roller bearing inner ring 36a toward the inner peripheral side from the outer peripheral side.

As shown in FIG. 18, the ultrasonic waves 4 are incident upon the rotating power roller bearing inner ring 36a at the angle of incidence of 0° from the end surface 75, and the normal beam probe 3b is moved in parallel with the end surface 75 toward the right from the left of the drawing. Where the incidence portion of the ultrasonic wave 4 reaches the corner edge of the end surface 75, the parallel movement of the probe 3b is stopped. Thereby, a second portion 66b is scanned in a range of a depth d3+d4 (=F/2) from the end surface 75 and about a half of the depth L2 from the inner peripheral surface 68 (about the half of the end surface 75 (e.g., 6 mm)).

Prior to the evaluation of the crack life (L10 life), the size and position of the defect were estimated as follows. The power roller bearing inner ring from which some defect echoes could be obtained was cut, the cut surface was observed in detail with the microscope, and thereby a relation (calibration) between the size (width and length) of the large nonmetal inclusion and the ultrasonic echo intensity was grasped. The calibration and measured defect echo were used to estimate the size and position of the defect which would be inside the member.

Table 5 shows the position and size of the defect (large nonmetal inclusion) detected beforehand in the input disk used in the crack life evaluation. These test materials were used to perform the simulation durability test of the apparatus with the toroidal CVT mounted thereon, and it was evaluated whether or not any crack was generated. Additionally, the disk and power roller bearing inner ring (other members) for use in materials other than the test materials used in the durability test underwent the ultrasonic inspection beforehand. It was confirmed that the amount of large nonmetal inclusions was smaller than that of test materials, and subsequently the members were used.

TABLE 5

| | Inspection result Power roller inner ring | | | | | |
|---|---|---|---|---|---|---|
| | Detected position of large inclusion | | Size of large inclusion | | | |
| Sample No. | Distance from end surface [depth direction] (mm) | Distance from inner peripheral surface (mm) | Width (mm) | Length (mm) | Square root length (mm) | Fatigue crack breakage time of power roller (Hr) |
| Sample 13 | F/11 | G/6.0 | 0.15 | 0.25 | 0.19 | 100 or more |
| Sample 14 | F/5.5 | G/2.0 | 0.20 | 0.20 | 0.20 | 100 or more |
| Sample 15 | F/3.4 | G/3.0 | 0.18 | 0.22 | 0.20 | 100 or more |
| Sample 16 | F/2.8 | G/3.4 | 0.12 | 0.30 | 0.19 | 100 or more |
| Sample 17 | F/2.0 | G/2.2 | 0.06 | 0.50 | 0.17 | 100 or more |
| Sample 18 | F/1.8 | G/6.0 | 0.24 | 0.25 | 0.24 | 100 or more |
| Sample 19 | F/1.5 | G/2.0 | 0.18 | 0.28 | 0.22 | 100 or more |
| Sample 20 | F/8.8 | G/1.8 | 0.24 | 0.30 | 0.27 | 100 or more |
| Sample 21 | F/2.2 | G/1.5 | 0.18 | 0.45 | 0.28 | 100 or more |
| Sample 22 | F/8.8 | G/5.2 | 0.20 | 0.23 | 0.21 | 66 |
| Sample 23 | F/11 | G/4 | 0.15 | 0.33 | 0.22 | 40 |

After the above-described treatment was performed, the surface of the power roller bearing was ground/processed, and used in the ultrasonic flaw detection.

Subsequently, for the power roller bearing inner ring, 11 test materials (e.g., Samples 13 to 23) were prepared, and the angle wave method and normal wave method were used to inspect the inner ring portion of each sample. The results are shown in Table 5. In the durability test, the time required until the power roller bearing inner ring as the test material cracked was checked Test conditions are as follows:

Rotation speed of input shaft; 4000 rpm

Input torque; 392 N·m (torque of maximum deceleration time)

Used oil; synthetic lubricant

Oil temperature; 100° C.

As apparent from Table 5, even when the detected position of the defect is in the diagonal-line region 66 of FIG. 8, but when the defect size is 0.20 mm or less in terms of the square root length, the crack was not generated even exceeding 100 hours, and the long life was found (Samples 13 to 17).

Moreover, even when the defect size exceeds 0.20 mm in terms of the square root length, but when the detected position is outside the diagonal-line region 66, the crack was not generated even exceeding 100 hours, and the long life was found (Samples 18 to 21). Additionally, the above-described parameter F is the total height size of the power roller bearing inner ring, and a parameter G is a size defined by G=(D−E)/2 in which the outer diameter of the vertex portion of the power roller bearing inner ring is D and the diameter of a hole 51 is E.

On the other hand, since the defect size in the diagonal-line region 66 exceeds the square root length of 0.20 mm in Samples 22 and 23 of Table 5, the materials crack in 66 hours and 40 hours, respectively, and have short lives.

Additionally, in Embodiments 1 to 4 described above, the single probe 3a was used in common with the surface wave method and angle wave method, and another probe 3b was used in the normal wave method. It is desirable to attach one set of these probes 3a, 3b to the arm 23, and the probes are preferably movably supported so as to change the angles of the respective ultrasonic oscillation surfaces on the arm 23. In this manner, a time to switch to the oblique angle flaw detection method from the surface wave method is shortened, a time to change to the second probe 3b from the first probe 3a is reduced, and the whole inspection time is largely reduced.

As described above, according to the present invention, not only the size of the large inclusion but also the influenced region in which the material exists are limited, and thereby higher-reliability components are provided. Since the ultrasonic inspection range is limited only to the influenced region, the total inspection can be performed in a short time.

Additionally, the inspection frequency of 15 MHz or less is preferable, and the present inventors have additionally confirmed that the similar results are obtained even with the use of the focus type probe of 10 MHz.

Moreover, in the above-described embodiments, the inner ring of the power roller bearing has been described, but the present invention is not limited to the inner ring, and the present invention can also be applied in parallel with the peripheral surface side in the rolling member holding groove in the outer ring of the power roller bearing.

According to the present invention, the portion of the toroidal CVT member in which destruction most easily occurs is inspected in a concentrated manner, and thereby the quality of the toroidal CVT member can be guaranteed with a high precision. Particularly when the optimum ultrasonic inspection is used in accordance with the depth from the surface, the inspection precision of the defect is dramatically enhanced, and the level of quality assurance can therefore be raised.

Moreover, according to the present invention, since the total number of toroidal CVT members are inspected, the high-reliability quality assurance is possible. Particularly since it is possible to grasp the true defect size and shape based on the echo reflected from the defect in the method of the present invention, the high reliability is obtained as compared with the conventional method of using the microscope to observe the defect appearing in the section in the two-dimensional manner.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A toroidal continuously variable transmission comprising: an input disk disposed on an input shaft; an output disk disposed on an output shaft; and a power roller bearing which includes an inner ring, an outer ring and a plurality of rolling members, in which said inner ring is rollingly contacted in said input disk and output disk and which transmits a power of said input shaft to said output shaft, wherein a maximum shear stress depth obtained on a condition on which said input disk is rollingly contacted in the inner ring of the power roller bearing in a maximum deceleration state of the toroidal continuously variable transmission and the power is transmitted is defined as a symbol Zo, a size of a defect obtained in accordance with a shape of the defect detected by a nondestructive inspection method is defined as a square root length, and then at least one of said input disk and said inner ring of the power roller bearing does not include a defect of 0.10 mm or more in terms of said square root length in a range of a depth from a traction surface which is twice the depth Zo.

2. The transmission according to claim 1, wherein at least one of said input disk and said inner ring of the power roller bearing does not include a defect of 0.05 mm or more in terms of the square root length in the range from said surface which is twice the depth Zo.

3. A method of: using at least one of an input disk and output disk of a toroidal continuously variable transmission as a rolling member; immersing an examination surface to be examined of the rolling member and a probe for ultrasonic flaw detection disposed opposite to the examination surface into an ultrasonic wave transmission medium; rotating the rolling member around an axial line; moving the probe for ultrasonic flaw detection forwards and backwards in a direction along the axial line in a section including the axial line of the rolling member; scanning the rolling member and the probe with respect to each other along a shape of the examination surface; propagating an ultrasonic wave to the rolling member from the probe via the medium; and evaluating defects which exist in the examination surface and an inner portion of the rolling member based on a waveform of ultrasonic echo reflected from the rolling member, comprising the steps of:

combining and using a first method of using either a surface wave method or angle wave method to scan the examination surface in a range right under the surface, and a second method of using either the angle wave method or a normal wave method to scan said examination surface right under the surface, and detecting a flaw within a depth range twice a maximum shear stress depth Zo; and judging the rolling member to be rejected, when a square root length of the detected defect is 0.05 mm or more.

4. A toroidal continuously variable transmission comprising: an input disk disposed on an input shaft; an output disk disposed on an output shaft; and a power roller bearing which includes an inner ring, an outer ring and a plurality of rolling members, in which said inner ring is engaged in said input disk and output disk and which transmits a power of said input shaft to said output shaft, wherein at least one of said input disk and output disk includes a disk center hole through which said input shaft or output shaft is passed, and does not include a defect exceeding 0.20 mm in terms of a square root length in a portion of a range which extends outwards in a radius direction from an inner peripheral surface of the disk center hole by a distance of ½ or less of a width of an end surface in a direction crossing at right angles to an axial line of the disk center hole, and in a direction along the axial line of the disk center hole from the end surface, in a depth of ⅓ or less of a disk width dimension.

5. A toroidal continuously variable transmission comprising: an input disk disposed on an input shaft; an output disk disposed on an output shaft; and a power roller bearing which includes an inner ring, an outer ring and a plurality of rolling members, in which said inner ring is engaged in said input disk and output disk and which transmits a power of said input shaft to said output shaft, wherein at least one of the inner ring and outer ring of said power roller bearing includes a tilting/rolling shaft hole through which a tilting/rolling shaft is passed, and does not include a defect exceeding 0.20 mm in terms of a square root length in a portion of a range which extends outwards in a radius direction from an inner peripheral surface by ½ or less of a distance to an inner peripheral surface of the tilting/rolling shaft hole from an inner edge groove of a rolling groove in an end surface, and in a direction along an axial line of the tilting/rolling shaft hole from the end surface, in a depth of ½ or less of a width dimension of the inner ring/outer ring.

6. A method of: using at least one of an input disk and output disk of a toroidal continuously variable transmission as a rolling member; immersing an examination surface to be examined of the rolling member and a probe for ultrasonic flaw detection disposed opposite to the examination surface into an ultrasonic wave transmission medium; rotating the rolling member around an axial line; moving the probe for ultrasonic flaw detection forwards and backwards along the axial line in a section including the axial line of the rolling member; scanning the rolling member and the probe with respect to each other along a shape of an end surface in a vertex of the disk as the examination surface; propagating an ultrasonic wave to the rolling member from the probe via the medium; and evaluating defects which exist in the examination surface and an inner portion of the rolling member based on a waveform of ultrasonic echo reflected from the rolling member, comprising the steps of:

combining and using a first method of using either a surface wave method or angle wave method to scan the examination surface in a range under the examination surface, and a second method of using either the angle wave method or a normal wave method to scan the examination surface under the surface, and detecting a flaw in a direction along the axial line of a disk center hole from said end surface, in a depth of ⅓ or less of a disk width dimension, in a direction crossing at right angles to the axial line of the disk center hole, and in a range of ½ or less of a width of the end surface; and judging the rolling member to be rejected, when the defect detected in a portion of a range extending outwards in a radius direction from an inner peripheral surface of said disk center hole exceeds 0.20 mm in terms of a square root length.

7. A method of: using at least one of an inner ring and outer ring of a power roller bearing as a rolling member; immersing an examination surface to be examined of the rolling member and a probe for ultrasonic flaw detection disposed opposite to the examination surface into an ultrasonic wave transmission medium; rotating the rolling member around an axial line; moving the probe forwards and backwards along the axial line in a section including the axial line of the rolling member; scanning the rolling member and the probe with respect to each other along a shape of an end surface as the examination surface on a side including a rolling groove; propagating an ultrasonic wave to the rolling member from the probe via the medium; and evaluating defects which exist in the examination surface and an inner portion of the rolling member based on a waveform of ultrasonic echo reflected from the rolling member, comprising the steps of:

combining and using a first method of using either a surface wave method or angle wave method to scan the examination surface in a range right under the surface, and a second method of using either the angle wave method or a normal wave method to scan said examination surface right under the surface, and detecting a flaw in a direction along the axial line of a tilting/rolling shaft hole from said end surface, in a depth of ½ or less of a width dimension of said inner/outer ring, and in a range of ½ or less of a distance to the inner peripheral surface of the tilting/rolling shaft hole from an inner edge groove of a rolling groove in the end surface; and judging the rolling member to be rejected, when the defect detected in a portion of a range extending outwards in a radius direction from an inner peripheral surface from said tilting/rolling shaft hole exceeds 0.20 mm in terms of a square root length.

8. A sliding rotation member which is rotatably supported by a support shaft in a toroidal continuously variable transmission, and slides on another member, wherein a maximum shear stress depth generated in a maximum deceleration state of the toroidal continuously variable transmission is defined as a symbol $Z_0$, a size of a defect obtained in accordance with a shape of the defect detected by a nondestructive inspection method is defined as a square root length, and then a defect of 0.10 mm or more in terms of said square root length is not included in a range of a depth from an examination surface which is twice the depth $Z_0$.

9. The sliding rotation member according to claim 8, wherein said examination surface is a traction surface which undergoes a dynamic repeated stress by mutual rolling contact with the another member.

10. The sliding rotation member according to claim 8, wherein said another member is an inner ring of a power roller bearing.

11. The sliding rotation member according to claim 8, wherein said another member is an input disk or an output disk.

12. A method of: immersing a sliding rotation member which is rotatably supported by a support shaft in a toroidal continuously variable transmission and slid on another member for use together with an ultrasonic probe into a transmission medium; allowing an ultrasonic wave to be incident upon the sliding rotation member from the ultrasonic probe via the transmission medium; and evaluating defects existing in an examination surface and an inner portion of the sliding rotation member based on a waveform of ultrasonic echo reflected from the sliding rotation member, said method comprising:

(a) a step of using at least one of a surface wave method and angle wave method to scan the examination surface of the sliding rotation member and a portion right under the examination surface;

(b) a step of defining a maximum shear stress depth generated inside the sliding rotation member at a maximum deceleration time of the toroidal continuously variable transmission as a symbol $Z_0$, and using at least one of the angle wave method and a normal wave method to scan a portion of a depth from the examination surface which is twice the depth $Z_0$; and (c) a step of defining a size of the defect obtained in accordance with a shape of the defect as a square root length, judging the sliding rotation member to be rejected, when said square root length of the defect detected by said steps (a) and (b) is 0.05 mm or more, and judging the sliding rotation member to be accepted, when said square root length of the defect detected in the steps (a) and (b) is less than 0.05 mm.

13. The method according to claim 12, wherein said steps (a) and (b) use the ultrasonic wave which has a predetermined frequency in a range of 5 MHz to 30 MHz.

14. The method according to claim 12, wherein said step (a) uses the ultrasonic wave which has a predetermined frequency in a range of 5 MHz to 15 MHz.

15. The method according to claim 12, wherein said step (b) uses the ultrasonic wave which has a predetermined frequency in a range of 10 MHz to 25 MHz.

* * * * *